United States Patent
Fujita et al.

(10) Patent No.: US 11,613,748 B2
(45) Date of Patent: Mar. 28, 2023

(54) METHOD FOR PRODUCING NUCLEIC ACID MOLECULE, BIOMATERIAL, AND METHOD FOR PRODUCING BIOMATERIAL

(71) Applicants: NEC Solution Innovators, Ltd., Tokyo (JP); MOSAIC BIOSCIENCES, INC., Boulder, CO (US)

(72) Inventors: Tomoko Fujita, Tokyo (JP); Iwao Waga, Tokyo (JP); Katsunori Horii, Tokyo (JP); Martin Stanton, Boulder, CO (US); Andrew Dalby, Boulder, CO (US)

(73) Assignees: NEC Solution Innovators, Ltd., Tokyo (JP); MOSAIC BIOSCIENCES, INC., Boulder, CO (US)

( * ) Notice: Subject to any disclaimer, the term of this patent is extended or adjusted under 35 U.S.C. 154(b) by 553 days.

(21) Appl. No.: 16/668,717

(22) Filed: Oct. 30, 2019

(65) Prior Publication Data
US 2021/0130820 A1    May 6, 2021

(51) Int. Cl.
C12N 15/113    (2010.01)
C12N 15/115    (2010.01)
C07K 14/705    (2006.01)
C12N 15/62    (2006.01)

(52) U.S. Cl.
CPC ...... *C12N 15/113* (2013.01); *C07K 14/70578* (2013.01); *C12N 15/115* (2013.01); *C12N 15/625* (2013.01)

(58) Field of Classification Search
None
See application file for complete search history.

(56) References Cited

FOREIGN PATENT DOCUMENTS

WO    2014/128289 A1    8/2014

OTHER PUBLICATIONS

Nomura et al., Devopment of functional biomaterials using RNA aptamer. Front. Biotechnol. Conference Abstract:10th World Biomaterials Congress. doi: 10.339/conf.FBIOE.2016.01.02676.*
Parisi et al., Aptamers vol. 1:3-12, 2017.*

International Search Report and Written Opinion, dated Jul. 28, 2020, issued by the International Searching Authority in International Application No. PCT/JP2020/018142.
Enam et al., "Enrichment of endogenous fractalkine and anti-inflammatory cells via aptamer-functionalized hydrogels", Biomaterials, 2017, vol. 142, pp. 52-61 (10 pages total).
Lee et al., "A therapeutic aptamer inhibits angiogenesis by specifically targeting the heparin binding domain of $VEGF_{165}$", PNAS, 2005, vol. 102, No. 52, pp. 18902-18907.
Napoleone Ferrara et al., "The biology of VEGF and its receptors", Nature Medicine, Jun. 2003, pp. 669-676, vol. 9, No. 6.
Maja Kenig et al., "Identification of the heparin-binding domain of TNF-alpha and its use for efficient TNF-alpha purification by heparin—Sepharose affinity chromatography", Journal of Chromatography B, 2008, pp. 119-125, vol. 867.
Pascale Garnier et al, "The localisation of the heparin binding sites of human and murine interleukin-12 within the carboxyterminal domain of the P40 subunit", Cytokine, 2018, pp. 159-168, vol. 110.
Shouchun Liu et al., "A heparin-binding synthetic peptide of heparin/heparan sulfate-interacting protein modulates blood coagulation activities", Proceedings of the National Academy of Sciences of the United States of America, Mar. 1997, pp. 1739-1744, vol. 94.
Shouchun Liu et al., "Heparin/Heparan Sulfate (HP/HS) Interacting Protein (HIP) Supports Cell Attachment and Selective, High Affinity Binding of HP/HS", The Journal of Biological Chemistry, Oct. 1997, pp. 25856-25862, vol. 272, No. 41.
Morishita Y., "Performance Report 2016 (project No. 15J10771)", Kakenhi-Project [online], Kaken, uploaded on Jan. 16, 2018 [retrieved on Jul. 14, 2020 from the internet: <URL: https://kaken.nii.ac.jp/report/KAKENHI-PROJECT-15J10771/15J107712016jissedki/>), 2 pages total.
Morishita Y., et al., 39th annual meeting abstract of Japan Society for Biomaterials, Nov. 13, 2017, vol. 39, p. 157 (IP-103-I), 2 pages total.

* cited by examiner

*Primary Examiner* — Sean McGarry
(74) *Attorney, Agent, or Firm* — Sughrue Mion, PLLC

(57) ABSTRACT

The present invention provides a method for producing a nucleic acid molecule that can obtain a nucleic acid molecule that binds to a target and does not inhibit a function of the target. The production method for a nucleic acid molecule of the present invention is a method for producing a nucleic acid molecule that binds to a first biological molecule and does not inhibit a function of the first biological molecule, the method including the steps of:
(A) bringing a candidate nucleic acid molecule into contact with the first biological molecule to select a nucleic acid molecule that has bound to the first biological molecule as a first selected nucleic acid molecule; and
(B) selecting the first selected nucleic acid molecule as an intended nucleic acid molecule.

2 Claims, 14 Drawing Sheets
Specification includes a Sequence Listing.

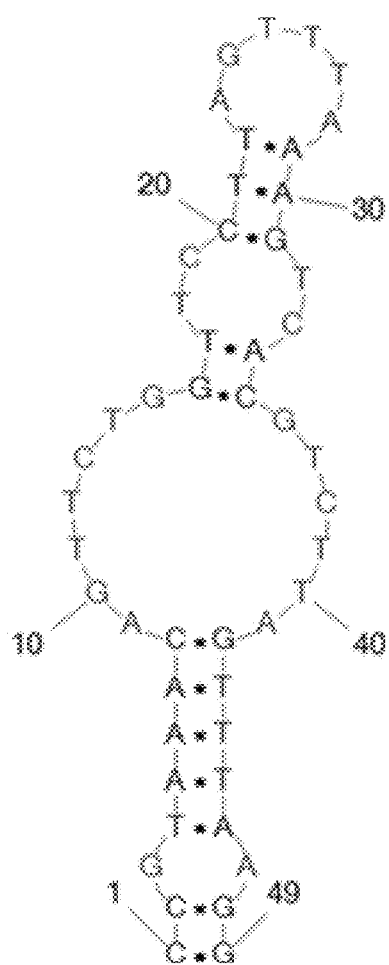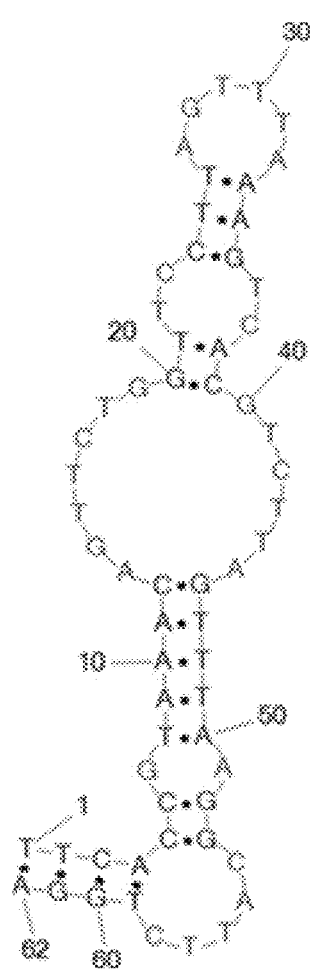
FIG. 1C     FIG. 1D
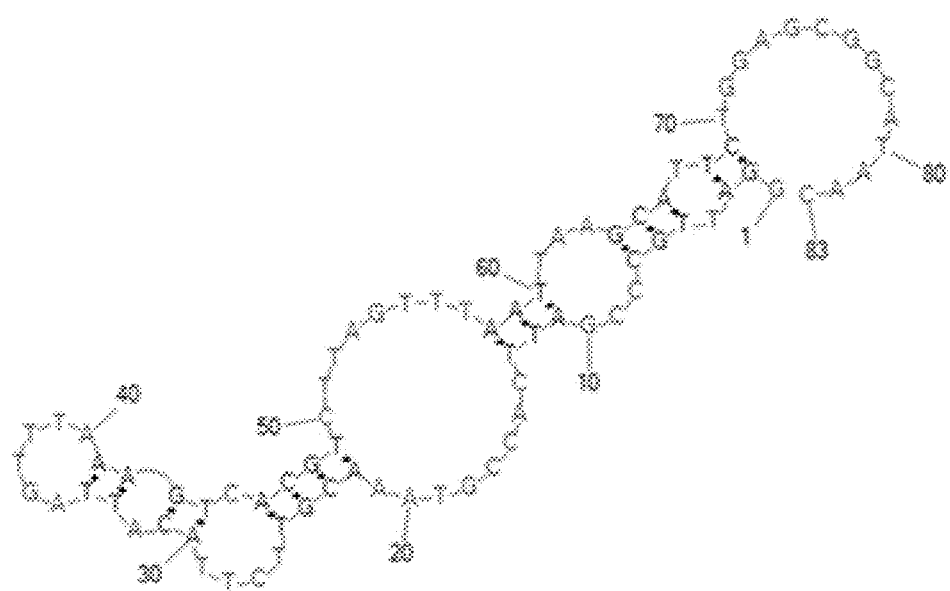
FIG. 1E

SEQUENCE LISTING

```
<160> NUMBER OF SEQ ID NOS: 14

<210> SEQ ID NO 1
<211> LENGTH: 83
<212> TYPE: DNA
<213> ORGANISM: Artificial Sequence
<220> FEATURE:
<223> OTHER INFORMATION: Synthetic polynucleotide sequence,
      VEGF746CaP_R8m1

<400> SEQUENCE: 1
ggattgcccg attcaccgta aacagttctg gttccttagt ttaaagtcac gtcttagttt      60
aaggcattct ggagcggcat aac                                             83

<210> SEQ ID NO 2
<211> LENGTH: 31
<212> TYPE: DNA
```

<213> ORGANISM: Artificial Sequence
<220> FEATURE:
<223> OTHER INFORMATION: Synthetic polynucleotide sequence,
      VEGF746CaP_5s31

<400> SEQUENCE: 2
ccttagttta aagtcacgtc ttagtttaag g                                    31

<210> SEQ ID NO 3
<211> LENGTH: 49
<212> TYPE: DNA
<213> ORGANISM: Artificial Sequence
<220> FEATURE:
<223> OTHER INFORMATION: Synthetic polynucleotide sequence,
      VEGF746CaP_5s49

<400> SEQUENCE: 3
ccgtaaacag ttctggttcc ttagtttaaa gtcacgtctt agtttaagg                 49

<210> SEQ ID NO 4
<211> LENGTH: 62
<212> TYPE: DNA
<213> ORGANISM: Artificial Sequence
<220> FEATURE:
<223> OTHER INFORMATION: Synthetic polynucleotide sequence,
      VEGF746CaP_5s62

<400> SEQUENCE: 4
ttcaccgtaa acagttctgg ttccttagtt taaagtcacg tcttagttta aggcattctg    60
ga                                                                   62

<210> SEQ ID NO 5
<211> LENGTH: 10
<212> TYPE: DNA
<213> ORGANISM: Artificial Sequence
<220> FEATURE:
<223> OTHER INFORMATION: Synthetic polynucleotide sequence

<400> SEQUENCE: 5
agtttaaagt                                                           10

<210> SEQ ID NO 6
<211> LENGTH: 8
<212> TYPE: DNA
<213> ORGANISM: Artificial Sequence
<220> FEATURE:
<223> OTHER INFORMATION: Synthetic polynucleotide sequence

<400> SEQUENCE: 6 agtttwad                                                              8

<210> SEQ ID NO 7
<211> LENGTH: 83
<212> TYPE: DNA
<213> ORGANISM: Artificial Sequence
<220> FEATURE:
<223> OTHER INFORMATION: Synthetic polynucleotide sequence,
      VEGF746CaP_R8m49

<400> SEQUENCE: 7
ggattgcccg attcaccgta aacgttctta cattagttta aagtcacgtc ttagtttaat    60
taagcattct ggagcggcat aac                                            83

<210> SEQ ID NO 8
<211> LENGTH: 101

```
<212> TYPE: PRT
<213> ORGANISM: Artificial Sequence
<220> FEATURE:
<223> OTHER INFORMATION: Synthetic peptide sequence, second Ig-like
      domain

<400> SEQUENCE: 8

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile
            100

<210> SEQ ID NO 9
<211> LENGTH: 67
<212> TYPE: PRT
<213> ORGANISM: Artificial Sequence
<220> FEATURE:
<223> OTHER INFORMATION: Synthetic peptide sequence, second Ig-like
      domain

<400> SEQUENCE: 9

Asn Lys Asn Lys Thr Val Val Ile Pro Cys Leu Gly Ser Ile Ser Asn
1               5                   10                  15

Leu Asn Val Ser Leu Cys Ala Arg Tyr Pro Glu Lys Arg Phe Val Pro
            20                  25                  30

Asp Gly Asn Arg Ile Ser Trp Asp Ser Lys Lys Gly Phe Thr Ile Pro
        35                  40                  45

Ser Tyr Met Ile Ser Tyr Ala Gly Met Val Phe Cys Glu Ala Lys Ile
    50                  55                  60

Asn Asp Glu
65

<210> SEQ ID NO 10
<211> LENGTH: 96
<212> TYPE: PRT
<213> ORGANISM: Artificial Sequence
<220> FEATURE:
<223> OTHER INFORMATION: Synthetic peptide sequence, third Ig-like
      domain

<400> SEQUENCE: 10

Asp Val Val Leu Ser Pro Ser His Gly Ile Glu Leu Ser Val Gly Glu
1               5                   10                  15

Lys Leu Val Leu Asn Cys Thr Ala Arg Thr Glu Leu Asn Val Gly Ile
            20                  25                  30

Asp Phe Asn Trp Glu Tyr Pro Ser Ser Lys His Gln His Lys Lys Leu
        35                  40                  45

Val Asn Arg Asp Leu Lys Thr Gln Ser Gly Ser Glu Met Lys Lys Phe
    50                  55                  60

Leu Ser Thr Leu Thr Ile Asp Gly Val Thr Arg Ser Asp Gln Gly Leu
```

```
                65                  70                  75                  80
Tyr Thr Cys Ala Ala Ser Ser Gly Leu Met Thr Lys Lys Asn Ser Thr
                    85                  90                  95
```

<210> SEQ ID NO 11
<211> LENGTH: 65
<212> TYPE: PRT
<213> ORGANISM: Artificial Sequence
<220> FEATURE:
<223> OTHER INFORMATION: Synthetic peptide sequence, exon 3

<400> SEQUENCE: 11

```
Val Lys Phe Met Asp Val Tyr Gln Arg Ser Tyr Cys His Pro Ile Glu
1               5                   10                  15

Thr Leu Val Asp Ile Phe Gln Glu Tyr Pro Asp Glu Ile Glu Tyr Ile
                20                  25                  30

Phe Lys Pro Ser Cys Val Pro Leu Met Arg Cys Gly Gly Cys Cys Asn
            35                  40                  45

Asp Glu Gly Leu Glu Cys Val Pro Thr Glu Glu Ser Asn Ile Thr Met
    50                  55                  60

Gln
65
```

<210> SEQ ID NO 12
<211> LENGTH: 26
<212> TYPE: PRT
<213> ORGANISM: Artificial Sequence
<220> FEATURE:
<223> OTHER INFORMATION: Synthetic peptide sequence, exon 4

<400> SEQUENCE: 12

```
Ile Met Arg Ile Lys Pro His Gln Gly Gln His Ile Gly Glu Met Ser
1               5                   10                  15

Phe Leu Gln His Asn Lys Cys Glu Cys Arg
                20                  25
```

<210> SEQ ID NO 13
<211> LENGTH: 55
<212> TYPE: PRT
<213> ORGANISM: Artificial Sequence
<220> FEATURE:
<223> OTHER INFORMATION: Synthetic peptide sequence, HBD

<400> SEQUENCE: 13

```
Ala Arg Gln Glu Asn Pro Cys Gly Pro Cys Ser Glu Arg Arg Lys His
1               5                   10                  15

Leu Phe Val Gln Asp Pro Gln Thr Cys Lys Cys Ser Cys Lys Asn Thr
                20                  25                  30

Asp Ser Arg Cys Lys Ala Arg Gln Leu Glu Leu Asn Glu Arg Thr Cys
            35                  40                  45

Arg Cys Asp Lys Pro Arg Arg
    50                  55
```

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide sequence

```
<400> SEQUENCE: 14

Lys Cys Gly Pro Gln Gly Ile Ala Gly Gln Cys Lys
1               5                   10
```

METHOD FOR PRODUCING NUCLEIC ACID MOLECULE, BIOMATERIAL, AND METHOD FOR PRODUCING BIOMATERIAL

BACKGROUND OF THE INVENTION

1. Field of the Invention

The present invention relates to a method for producing a nucleic acid molecule, a biomaterial, and a method for producing a biomaterial.

2. Description of Related Art

Growth factors are endogenous proteins that stimulate cell proliferation and differentiation. It is known that a vascular endothelial growth factor (VEGF), which is one of the growth factors, binds as a ligand to a vascular endothelial growth factor receptor (VEGFR), thereby being involved in angiogenesis etc. (Non-Patent Document 1).

On the other hand, nucleic acid molecules that specifically bind to a target such as a protein are attracting attention.

CITATION LIST

Patent Document(s)

[Non-Patent Document 1] Ferrara N. et al., Nat Med., 2003 June; 9(6): 669-76.

SUMMARY OF THE INVENTION

However, heretofore, there has been a case in which the nucleic acid molecule inhibits the function of the target by binding to the target.

With the foregoing in mind, it is an object of the present invention to provide a method for producing a nucleic acid molecule that can obtain a nucleic acid molecule that binds to a target and does not inhibit a function of the target.

In order to achieve the above object, the present invention provides a method for producing a nucleic acid molecule that binds to a first biological molecule and does not inhibit a function of the first biological molecule, the method including the steps of:
(A) bringing a candidate nucleic acid molecule into contact with the first biological molecule to select a nucleic acid molecule that has bound to the first biological molecule as a first selected nucleic acid molecule; and
(B) selecting the first selected nucleic acid molecule as an intended nucleic acid molecule.

The present invention also provides a nucleic acid molecule that binds to VEGF, the nucleic acid molecule including:
any one of the following polynucleotides (a) and (b):
(a) a polynucleotide that consists of a base sequence of SEQ ID NO: 1 or a partial sequence of the base sequence of SEQ ID NO: 1; and
(b) a polynucleotide that consists of a base sequence having at least 80% identity to the base sequence of the polynucleotide (a), binds to VEGF, and does not inhibit a function of the VEGF.

The present invention also provides a biomaterial including:
a binding nucleic acid molecule; and
a carrier,
the binding nucleic acid molecule being bound to the carrier, wherein the binding nucleic acid molecule binds to a predetermined protein and does not inhibit a function of the predetermined protein.

The present invention also provides a method for producing a biomaterial, the method including the step of:
binding a binding nucleic acid molecule to a carrier, wherein the binding nucleic acid molecule binds to a predetermined protein and does not inhibit a function of the predetermined protein.

Effects of Invention

The present invention can provide a method for producing a nucleic acid molecule that can obtain a nucleic acid molecule that binds to a target and does not inhibit a function of the target.

BRIEF DESCRIPTION OF THE DRAWINGS

FIGS. 1A to 1E show the predicted secondary structures of aptamers 1 to 5 (SEQ ID NOs: 1-4 and 7), respectively.

DETAILED DESCRIPTION OF THE INVENTION

Figure 1A:
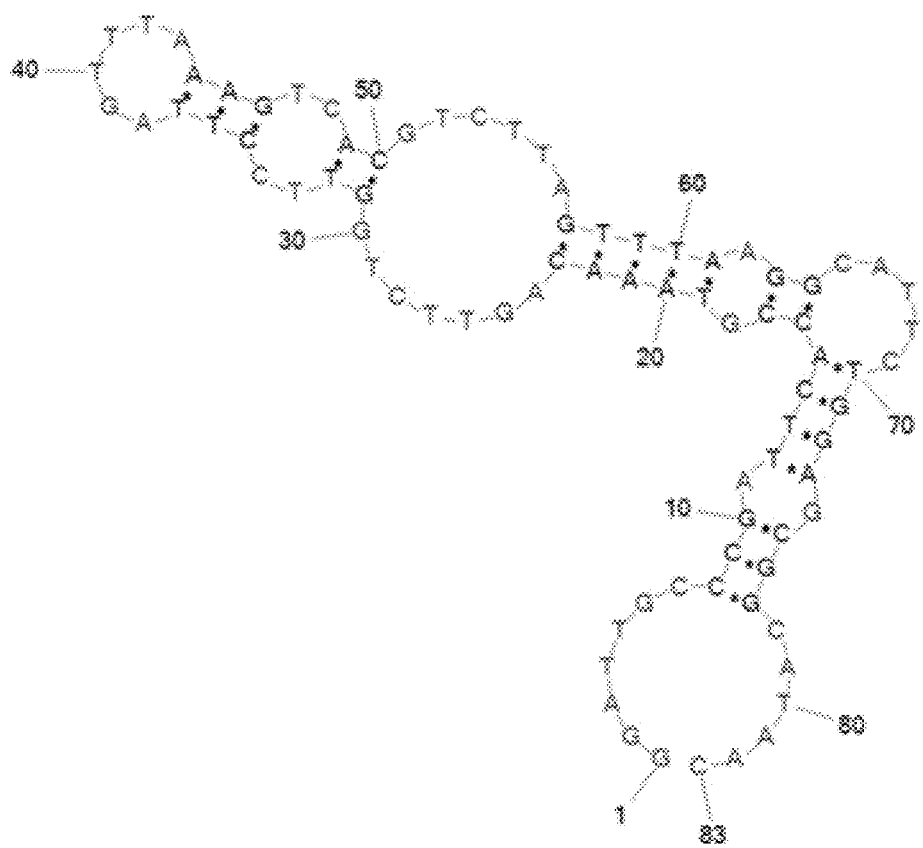
Figure 1B:
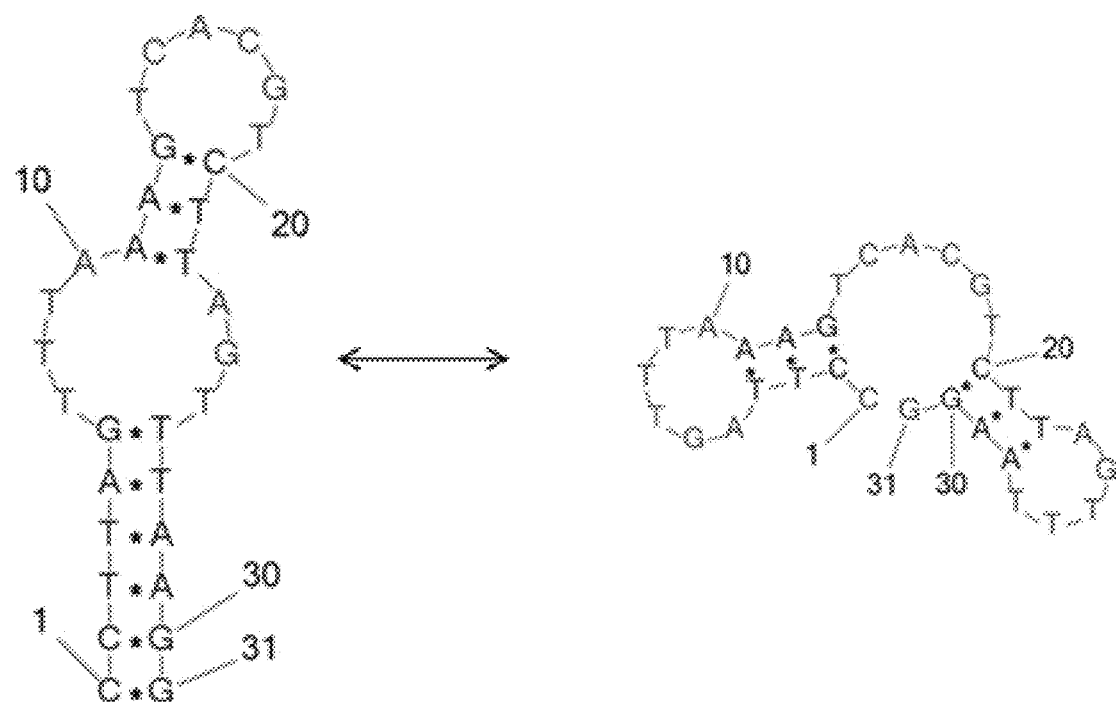

Hereinafter, the present invention will be described by way of example embodiments. It is to be noted, however, that the present invention is not limited to the following example embodiments. Unless otherwise stated, the descriptions regarding the respective example embodiments may be referenced to each other.

First Example Embodiment (1) Nucleic Acid Molecule

The nucleic acid molecule of the present invention is, as described above, a nucleic acid molecule that binds to VEGF, including: any one of the following polynucleotides (a) and (b):
(a) a polynucleotide that consists of a base sequence of SEQ ID NO: 1 or a partial sequence of the base sequence of SEQ ID NO: 1; and
(b) a polynucleotide that consists of a base sequence having at least 80% identity to the base sequence of the polynucleotide (a), binds to VEGF, and does not inhibit a function of the VEGF.

In the present invention, a vascular endothelial growth factor (VEGF) is a target. The binding ability of the nucleic acid molecule of the present invention to VEGF can be checked using a commercially available VEGF, for example. A specific example of the commercially available VEGF is a VEGF165 (PeproTech, Cat: 100-20). In the present invention, VEGF165 also may be referred to simply as "VEGF" hereinafter.

The nucleic acid molecule of the present invention can bind to VEGF, as described above. In the present invention, the expression "binds to VEGF" (and grammatical variations thereof) also is referred to as "has binding properties to VEGF" or "has binding activity to VEGF", for example. The binding between the nucleic acid molecule of the present invention and VEGF can be determined by surface plasmon resonance (SPR) analysis or the like, for example. The analysis can be performed using a BIACORE 3000 (trade name, GE Healthcare UK Ltd.), for example. Since the nucleic acid molecule of the present invention binds to VEGF, it can be used for detection of VEGF, for example.

The dissociation constant, which indicates the binding force, of the nucleic acid molecule of the present invention to VEGF is, for example, $1.71\times10^{-17}$, $4.73\times10^{-21}$, $1.07\times10^{-10}$, $7.35\times10^{-15}$, or $2.45\times10^{-17}$ mol/L in the absence of calcium ions and $1.43\times10^{-16}$, $3.66\times10^{-17}$, $2.17\times10^{-21}$, $3.32\times10^{-16}$, or $2.16\times10^{-16}$ mol/L in the presence of calcium ions.

The nucleic acid molecule of the present invention also is referred to as a DNA molecule or a DNA aptamer. The nucleic acid molecule of the present invention may be a molecule consisting of or including the polynucleotide (a) or (b), for example.

The polynucleotide (a) may be, for example, a polynucleotide including or consisting of the base sequence of SEQ ID NO: 1 or a polynucleotide including or consisting of a partial sequence of the base sequence of SEQ ID NO: 1. The polynucleotide consisting of the base sequence of SEQ ID NO: 1 is shown below. In the base sequence of SEQ ID NO: 1 and base sequences of SEQ ID NOs: 2 to 4 and 7 to be described below, sequences corresponding to motif sequences (SEQ ID NOs: 5 and 6) to be described below are underlined.

VEGF746CaP_R8m1

(SEQ ID NO: 1)
GGATTGCCCGATTCACCGTAAACAGTTCTGGTTCCTT<u>AGTTTAAAGTCA</u>
CGTCTT<u>AGTTTAAGG</u>CATTCTGGAGCGGCATAAC

In sequence analysis performed after nucleic acid molecule selection according to the SELEX method, for example, the base sequence of SEQ ID NO: 1 is present at a frequency of 6.2% in all the sequences. In the sequence analysis, for example, when a predetermined sequence is present at a frequency of 5% or more in all the sequences, it can be determined that the sequence has been enriched sufficiently by the selection.

The partial sequence is not particularly limited, and examples thereof include the base sequences of SEQ ID NOs: 2 to 4.

VEGF746_CaP_5s31

(SEQ ID NO: 2)
CCTT<u>AGTTTAAAGT</u>CACGTCTT<u>AGTTTAAGG</u>

VEGF746_CaP_5s49

(SEQ ID NO: 3)
CCGTAAACAGTTCTGGTTCCTT<u>AGTTTAAAGT</u>CACGTCTT<u>AGTTTAAGG</u>

VEGF746_CaP_5s62

(SEQ ID NO: 4)
TTCACCGTAAACAGTTCTGGTTCCTT<u>AGTTTAAAGT</u>CACGTCTT<u>AGTTTA</u>

<u>A</u>GGCATTCTGGA

Regarding the polynucleotide (b), the "identity" is not particularly limited as long as it is in a range where the polynucleotide (b) binds to VFGF, for example. The identity is, for example, at least 80%, preferably at least 85%, more preferably at least 90%, still more preferably at least 95%, at least 96%, and at least 97%, particularly preferably at least 98%, and most preferably at least 99%. The identity can be calculated with analysis software such as BLAST or FASTA using default parameters, for example (the same applies hereinafter).

Regarding the polynucleotide (b), the "function of the VEGF" is, for example, a function of binding to a VEGF receptor. Also, the "function of the VEGF" is, for example, a function of regulating activity of the VEGF receptor by binding to the VEGF receptor.

The polynucleotide (b) may be the following polynucleotide (b1), for example. In this case, the nucleic acid molecule of the present invention may be a molecule consisting of or including the polynucleotide (b1), for example.

(b1) a polynucleotide that consists of a base sequence having at least 80% identity to the base sequence of the polynucleotide (a), includes a base sequence of any one of SEQ ID NOs: 2 to 4, binds to the VEGF, and does not inhibit the function of the VEGF.

The polynucleotide in the nucleic acid molecule of the present invention may be the following polynucleotide (b2), for example. In this case, the nucleic acid molecule of the present invention may be a molecule consisting of or including the polynucleotide (b2), for example.

(b2) a polynucleotide that consists of a base sequence having at least 80% identity to the base sequence of the polynucleotide (a), can form a secondary structure represented by any one of the following formulae (1) to (5), binds to the VEGF, and does not inhibit the function of the VEGF.

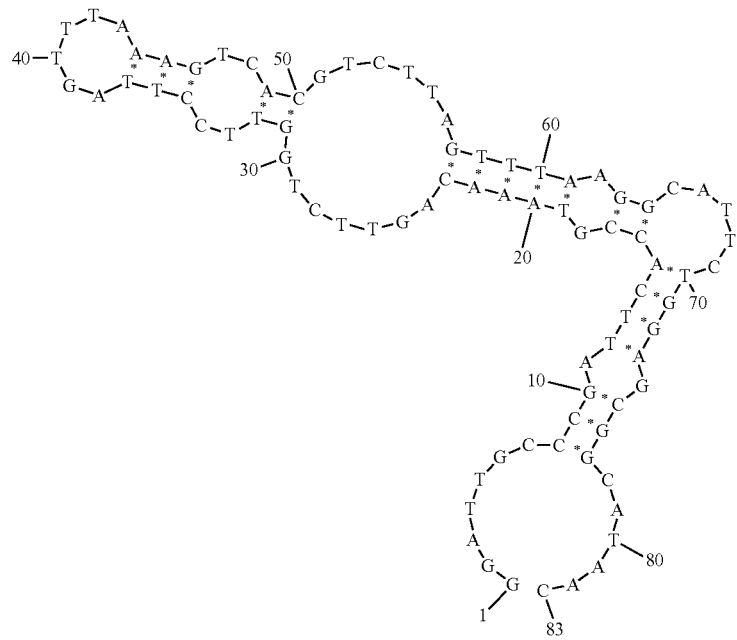
(1)
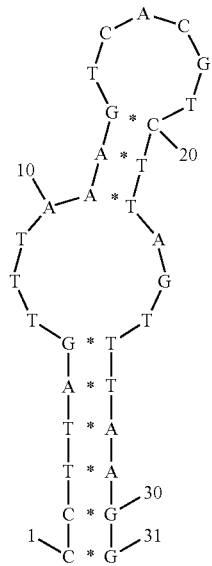
(2)
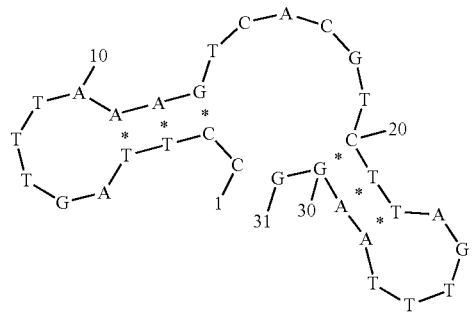
(3)

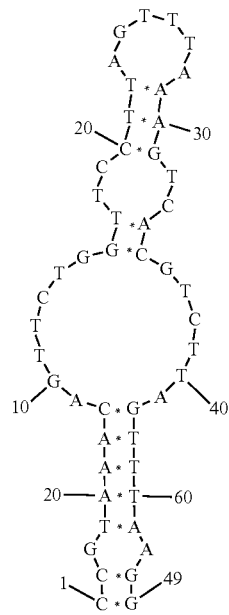

(4)

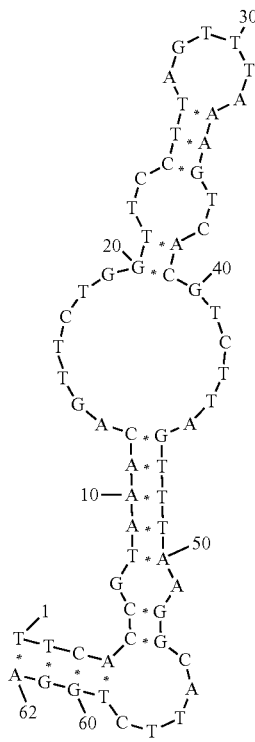

(5)

Regarding the above formulae, the formula (1) corresponds to SEQ ID NO: 1, the formulae (2) and (3) correspond to SEQ ID NO: 2, the formula (4) corresponds to SEQ ID NO: 3, and the formula (5) corresponds to SEQ ID NO: 4. It is speculated that the secondary structures represented by the formulae (2) and (3) are in equilibrium. It is to be noted, however, that the present invention is not limited thereto.

Specifically, the polynucleotide (b2) is, for example: a polynucleotide that consists of a base sequence having at least 80% identity to the base sequence of SEQ ID NO: 1, can form the secondary structure represented by the formula (1), binds to the VEGF, and does not inhibit the function of the VEGF; a polynucleotide that consists of a base sequence having at least 80% identity to the base sequence of SEQ ID NO: 2, can form the secondary structure represented by the formula (2) or (3), binds to the VEGF, and does not inhibit the function of the VEGF; a polynucleotide that consists of a base sequence having at least 80% identity to the base sequence of SEQ ID NO: 3, can form the secondary structure represented by the formula (4), binds to the VEGF, and does not inhibit the function of the VEGF; or a polynucleotide that consists of a base sequence having at least 80% identity to the base sequence of SEQ ID NO: 4, can form the secondary structure represented by the formula (5), binds to the VEGF, and does not inhibit the function of the VEGF.

Specifically, the polynucleotide (b2) is, for example, a polynucleotide that consists of a base sequence having at least 80% identity to the base sequence of SEQ ID NO: 1, can form the secondary structure represented by any one of the formulae (2) to (5), binds to the VEGF, and does not inhibit the function of the VEGF.

Regarding the polynucleotide (b2), the expression "can form a secondary structure" means that, for example, the polynucleotide (b2) can form the stem structure and the loop structure represented by the above formulae. The stem structure and the loop structure will be described below.

The polynucleotide in the nucleic acid molecule of the present invention may be the following polynucleotide (b3), for example. In this case, the nucleic acid molecule of the present invention may be a molecule consisting of or including the polynucleotide (b3), for example.

(b3) a polynucleotide that consists of a base sequence having at least 80% identity to the base sequence of the polynucleotide (a), includes a base sequence of at least one of SEQ ID NOs: 5 and 6, binds to the VEGF, and does not inhibit the function of the VEGF.

SEQ ID NO: 5
AGTTTAAAGT

SEQ ID NO: 6
AGTTTWAD

In the above sequence, W indicates adenine or thymine, and D indicates adenine, guanine, or thymine.

Specifically, the polynucleotide (b3) is, for example, a polynucleotide that consists of a base sequence having at least 80% identity to any one of the base sequences of SEQ ID NOs: 1 to 4, includes a base sequence of at least one of SEQ ID NOs: 5 and 6, binds to the VEGF, and does not inhibit the function of the VEGF.

The base sequences of SEQ ID NOs: 5 and 6 are motif sequences in the base sequences of SEQ ID NOs: 1 to 4 and 7, for example. The motif sequences were determined by performing alignment analysis with respect to sequences present at a frequency of 5% or more in all the sequences in the sequence analysis performed after nucleic acid molecule selection according to the SELEX method.

The polynucleotide in the nucleic acid molecule of the present invention may be the following polynucleotide (b4), for example. In this case, the nucleic acid molecule of the present invention may be a molecule consisting of or including the polynucleotide (b4), for example.

(b4) a polynucleotide that consists of a base sequence having at least 80% identity to the base sequence of the polynucleotide (a), can form a secondary structure represented by at least one of the following formulae (6) to (8), binds to the VEGF, and does not inhibit the function of the VEGF.

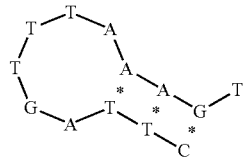
(6)

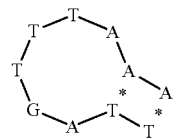
(7)

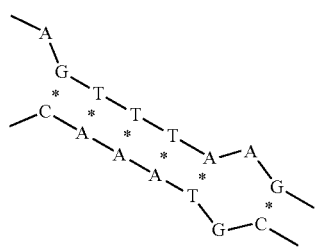
(8)

The formula (6) shows the secondary structure corresponding to the base sequence of SEQ ID NO: 5. The formulae (7) and (8) show the secondary structures corresponding to the base sequence of SEQ ID NO: 6. In the formulae (6) to (8), bases corresponding to SEQ ID NOs: 5 and 6 are indicated in boldface.

Specifically, the polynucleotide (b4) is, for example: a polynucleotide that consists of a base sequence having at least 80% identity to the base sequence of SEQ ID NO: 1, can form the secondary structure of the formula (6) or (7) and the secondary structure of the formula (8), binds to the VEGF, and does not inhibit the function of the VEGF; a polynucleotide that consists of a base sequence having at least 80% identity to the base sequence of SEQ ID NO: 2, can form the secondary structure of the formula (6) or (7), binds to the VEGF, and does not inhibit the function of the VEGF; a polynucleotide that consists of a base sequence having at least 80% identity to the base sequence of SEQ ID NO: 3, can form the secondary structure of the formula (6) or (7) and the secondary structure of the formula (8), binds to the VEGF, and does not inhibit the function of the VEGF; or a polynucleotide that consists of a base sequence having at least 80% identity to the base sequence of SEQ ID NO: 4, can form the secondary structure the formula (6) or (7) and the secondary structure of the formula (8), binds to the VEGF, and does not inhibit the function of the VEGF.

The polynucleotide (b) may be a polynucleotide consisting of the base sequence of SEQ ID NO: 7, for example. The base sequence of SEQ ID NO: 7 is a base sequence having 89.5% identity to the base sequence of SEQ ID NO: 1.

VEGF746CaP_R8m49
SEQ ID NO: 7)
GGATTGCCCGATTCACCGTAAACGTTCTTACATT<u>AGTTTAAAGT</u>CACGTC

TT<u>AGTTTAAT</u>TAAGCATTCTGGAGCGGCATAAC

The base sequence of SEQ ID NO: 7 can form a secondary structure represented by the following formula (10). The base sequence of SEQ ID NO: 7 includes the base sequences of SEQ ID NOs: 5 and 6. The base sequence of SEQ ID NO: 7 can form a secondary structure represented by the formula (7).

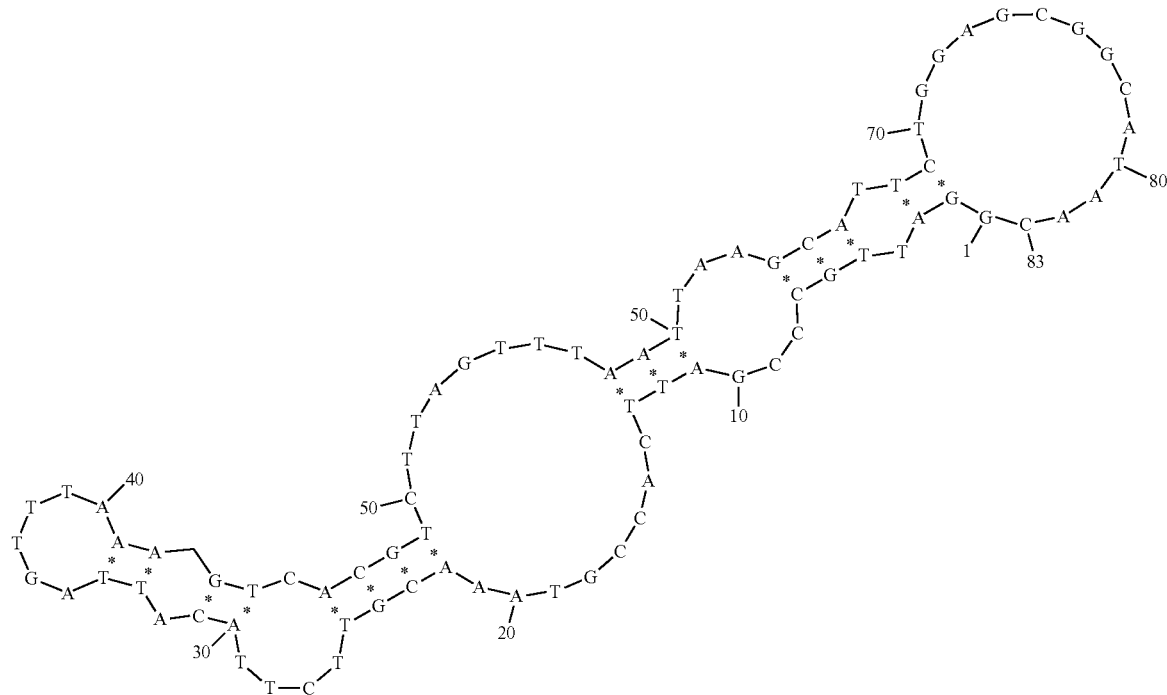
(10)

The polynucleotide in the nucleic acid molecule of the present invention may be the following polynucleotide (c), for example. In this case, the nucleic acid molecule of the present invention may be a molecule consisting of or including the polynucleotide (c), for example. (c) a polynucleotide that consists of a base sequence complementary to a polynucleotide hybridizing to the base sequence of the polynucleotide (a) under stringent conditions, binds to VEGF, and does not inhibit a function of the VEGF.

Regarding the polynucleotide (c), the "polynucleotide hybridizing to" is not particularly limited, and is, for example, a polynucleotide perfectly or partially complementary to the base sequence of the polynucleotide (a). The hybridization can be detected by various types of hybridization assay, for example. The hybridization assay is not particularly limited. For example, it is possible to employ a method described in "Molecular Cloning: A Laboratory Manual $2^{nd}$ Ed." edited by Sambrook et al. (Cold Spring Harbor Laboratory Press [1989]) or the like.

Regarding the polynucleotide (c), the "stringent conditions" may be any of low stringency conditions, moderate stringency conditions, and high stringency conditions, for example. The "low stringency conditions" are, for example, conditions where 5×SSC, 5×Denhardt's solution, 0.5% SDS, and 50% formamide are used at 32° C. The "moderate stringency conditions" are, for example, conditions where 5×SSC, 5×Denhardt's solution, 0.5% SDS, and 50% formamide are used at 42° C. The "high stringency conditions" are, for example, conditions where 5×SSC, 5×Denhardt's solution, 0.5% SDS, and 50% formamide, are used at 50° C. Those skilled in the art can set the degree of stringency by, for example, setting the conditions such as the temperature, the salt concentration, the concentration and length of a probe, the ionic strength, the time, etc. as appropriate. As the "stringent conditions", it is also possible to employ conditions described in the above-described "Molecular Cloning: A Laboratory Manual $2^{nd}$ Ed." edited by Sambrook et al. (Cold Spring Harbor Laboratory Press [1989]) or the like, for example.

The polynucleotide in the nucleic acid molecule of the present invention may be the following polynucleotide (d), for example. In this case, the nucleic acid molecule of the present invention may be a molecule consisting of or including the polynucleotide (d), for example. (d) a polynucleotide that consists of a base sequence obtained by deletion, substitution, insertion, and/or addition of one or more bases in the base sequence of the polynucleotide (a), binds to VEGF, and does not inhibit a function of the VEGF.

Regarding the polynucleotide (d), the phrase "one or more" is not limited as long as, for example, it is in a range where the polynucleotide (d) binds to VEGF. The "one or more" bases in the base sequence of the polynucleotide (a) are, for example, 1 to 10 bases, preferably 1 to 7 bases, more preferably 1 to 5 bases, still more preferably 1 to 3 bases, and particularly preferably 1 base or 2 bases. In the present invention, the numerical range regarding the number of bases, sequences, or the like discloses, for example, all the positive integers falling within that range. That is, for example, the description "one to five bases" discloses all of "one, two, three, four, and five bases" (the same applies hereinafter).

The nucleic acid molecule may include, for example, any one sequence selected from the polynucleotides (a) to (d), or a plurality of sequences selected from the polynucleotides (a) to (d). In the latter case, it is preferable that the plurality of polynucleotide sequences are linked to each other to form a single-stranded polynucleotide. The plurality of polynucleotide sequences may be linked to each other directly, or may be linked to each other indirectly with a linker, for example. It is preferable that the polynucleotide sequences are linked to each other directly or indirectly at their ends. The plurality of polynucleotide sequences may be the same or different from each other, for example. Preferably, they are the same. When the nucleic acid molecule of the present invention includes the plurality of polynucleotide sequences, the number of the sequences is not particularly limited, and is, for example, 2 or more, preferably 2 to 12, more preferably 2 to 6, and still more preferably 2.

The linker is a polynucleotide, for example. The building blocks of the linker are nucleotide residues, for example. Examples of the nucleotide residues include ribonucleotide residues and deoxyribonucleotide residues, for example. The length of the linker is not particularly limited, and is, for example, 1- to 24-mer, preferably 12- to 24-mer, more preferably 16- to 24-mer, and still more preferably 20- to 24-mer.

In the nucleic acid molecule of the present invention, the polynucleotide preferably is a single-stranded polynucleotide. It is preferable that the single-stranded polynucleotide can form a stem structure and a loop structure by self-annealing, for example. It is preferable that the polynucleotide can form a stem-loop structure, an internal loop structure, and/or a bulge structure, for example.

The nucleic acid molecule may be a double strand, for example. When the nucleic acid molecule is a double strand, for example, one of single-stranded polynucleotides is any of the polynucleotides (a) to (d), and the other single-stranded polynucleotide is not limited. The other single-stranded polynucleotide may be, for example, a polynucleotide consisting of a base sequence complementary to any of the polynucleotides (a) to (d). When the nucleic acid molecule of the present invention is a double strand, it is preferable to dissociate the double strand to single-stranded polynucleotides by denaturation or the like before use, for example. Also, it is preferable that the dissociated single-stranded polynucleotide, which is any of the polynucleotides (a) to (d), is forming a stem structure and a loop structure as described above, for example.

In the present invention, the expression "can form a stem structure and a loop structure" encompasses that, for example, a stem structure and a loop structure are formed actually, and also, even if a stem structure and a loop structure are not formed, they can be formed depending on conditions. The expression "can form a stem structure and a loop structure" encompasses, for example, both the cases where the formation thereof has been confirmed through an experiment and where the formation thereof is predicted through simulation using a computer or the like.

The length of the nucleic acid molecule is not particularly limited. The lower limit of the length is, for example, 15-mer, 75-mer, or 80-mer, and the upper limit of the length is, for example, 1000-mer, 200-mer, 100-mer, or 90-mer.

The building blocks of the nucleic acid molecule are nucleotide residues, for example. Examples of the nucleotide residues include deoxyribonucleotide residues and ribonucleotide residues. Examples of the nucleic acid molecule of the present invention include DNA consisting of deoxyribonucleotide residues only and DNA including one or more ribonucleotide residues. In the latter case, the phrase "one or more" is not particularly limited. For example, the number of the ribonucleotide residues in the polynucleotide is, for example, 1 to 3.

The polynucleotide may include a modified base(s). The modified base is not particularly limited, and may be, for example, a modified natural base (non-artificial base), which preferably has a similar function to the natural base. The natural base is not particularly limited, and may be, for example, a purine base with a purine skeleton, a pyrimidine base with a pyrimidine skeleton, or the like. The purine base is not particularly limited, and examples thereof include adenine (a) and guanine (g). The pyrimidine base is not particularly limited, and examples thereof include cytosine (c), thymine (t), and uracil (u). The modified site in the base is not particularly limited. When the base is a purine base, the modified site in the purine base is the 7-position or the 8-position in the purine skeleton, for example. When the base is a pyrimidine base, the modified site in the pyrimidine base is the 5-position or the 6-position in the pyrimidine skeleton, for example. When the pyrimidine skeleton has "=O" bound to the carbon at the 4-position and a group that is not "—$CH_3$" or "—H" bound to the carbon at the 5-position, the modified base can be referred to as modified uracil or modified thymine.

The nucleic acid molecule of the present invention may include, for example, one or more artificial nucleic acid monomer residues. The phrase "one or more" is not particularly limited, and may be, for example, 1 to 80, preferably 1 to 70, more preferably 1 to 50, still more preferably 1 to 40, particularly preferably 1 to 30, and most preferably 1 to 21 in the polynucleotide. The artificial nucleic acid monomer residue is, for example, a peptide nucleic acid (PNA), a locked nucleic acid (LNA), or a 2'-O,4'-C-ethylenebridged nucleic acid (ENA). The nucleic acid in the monomer residue is the same as described above, for example. The number of the artificial nucleic acid monomer residues in the full length of the nucleic acid molecule including the polynucleotide also is not particularly limited, and is, for example, the same as those described above.

It is preferable that the nucleic acid molecule of the present invention is resistant to nuclease, for example. In order to allow the nucleic acid molecule to have nuclease resistance, it is preferable that the nucleic acid molecule of the present invention includes the modified nucleotide residue(s) and/or the artificial nucleic acid monomer residue(s), for example. Also, in order to allow the nucleic acid molecule to have nuclease resistance, the nucleic acid molecule of the present invention may have polyethylene glycol (PEG) of several tens of kDa, deoxythymidine, or the like bound to the 5' end or the 3' end thereof, for example.

The nucleic acid molecule of the present invention may further include an additional sequence, for example. Preferably, the additional sequence is bound to at least one of the 5' end and the 3' end, more preferably to the 3' end of the nucleic acid molecule, for example. The additional sequence is not particularly limited. The length of the additional sequence is not particularly limited, and is, for example, 1- to 200-mer, preferably 1- to 50-mer, more preferably 1- to 25-mer, and still more preferably 18- to 24-mer. The building blocks of the additional sequence are, for example, nucleotide residues, examples of which include deoxyribonucleotide residues and ribonucleotide residues. The additional sequence is not particularly limited, and examples thereof include polynucleotides such as DNA consisting of deoxyribonucleotide residues and DNA including a ribonucleotide residue(s). Specific examples of the additional sequence include poly(dT) and poly(dA).

The nucleic acid molecule of the present invention can be used in the state where it is immobilized on a carrier, for example. For example, either the 5' end or the 3' end of the nucleic acid molecule of the present invention may be immobilized. When the nucleic acid molecule of the present invention is immobilized, the nucleic acid molecule may be immobilized either directly or indirectly to the carrier, for example. In the latter case, it is preferable to immobilize the nucleic acid molecule via the additional sequence, for example. The carrier may be beads, a plate, a filter, a column, a substrate, or a container, for example.

The nucleic acid molecule of the present invention may further include a labeling substance, for example. Specifically, the nucleic acid molecule may have the labeling substance bound thereto. The nucleic acid molecule having the labeling substance bound thereto also can be referred to as a nucleic acid sensor of the present invention, for example. The labeling substance may be bound to at least one of the 5' end and the 3' end of the nucleic acid molecule, for example. Labelling with the labeling substance may be achieved through binding or chemical modification, for example. The labeling substance is not particularly limited, and is, for example, an enzyme, a fluorescent substance, a dye, an isotope, a drug, a toxin, or an antibiotic. Examples of the enzyme include luciferase and SA-Lucia luciferase. Examples of the fluorescent substance include fluorophores such as pyrene, TAMRA, fluorescein, a Cy3 dye, a Cy5 dye, a FAM dye, a rhodamine dye, a Texas Red dye, JOE, MAX, HEX, and TYE. Examples of the dye include Alexa dyes such as Alexa 488 and Alexa 647. The labeling substance may be linked to the nucleic acid molecule directly, or indirectly via a linker, for example. The linker is not particularly limited, and may be a polynucleotide, for example.

The method for producing the nucleic acid molecule of the present invention is not particularly limited. For example, the nucleic acid molecule of the present invention can be synthesized by known methods such as: nucleic acid synthesis utilizing chemical synthesis methods; and genetic engineering procedures. The nucleic acid molecule of the present invention can be produced by, for example, a method for producing a nucleic acid molecule according to the present invention to be described below.

The nucleic acid molecule of the present invention exhibits binding properties to VEGF, as described above. Thus, use of the nucleic acid molecule of the present invention is not particularly limited, as long as it is the use utilizing the binding properties of the nucleic acid molecule to VEGF. The nucleic acid molecule of the present invention can be used in various methods as a substitute for, e.g., an antibody against VEGF.

The nucleic acid molecule of the present invention can detect VEGF. The method for detecting VEGF is not particularly limited, and VEGF can be detected by detecting the binding between the VEGF and the nucleic acid molecule.

(2) Detection Reagent and Kit

A detection reagent of the present invention is a reagent for detecting VEGF, characterized in that it contains the nucleic acid molecule of the present invention. It is only necessary that the detection reagent of the present invention contains the nucleic acid molecule of the present invention, and other configurations are not limited by any means. With the use of the detection reagent of the present invention, it is possible to detect VEGF as described above, for example. The detection reagent of the present invention also can be referred to as a binding agent to VEGF, for example.

The detection reagent of the present invention may further contain a labeling substance, and the labeling substance may be bound to the nucleic acid molecule, for example. For example, the description regarding the labeling substance provided above in connection with the nucleic acid molecule of the present invention also applies to the labeling substance in the detection reagent. Also, the detection reagent of the present invention may further contain a carrier, and the nucleic acid molecule may be immobilized on the carrier, for example. For example, the description regarding the carrier provided above in connection with the nucleic acid molecule of the present invention also applies to the carrier in the detection reagent.

A detection kit of the present invention includes the nucleic acid molecule of the present invention or the detection reagent of the present invention. The detection kit of the present invention may further include a component(s) in addition to the nucleic acid molecule or the detection reagent of the present invention, for example. Examples of the component include a buffer solution for preparing a sample and instructions for use. In the case where a detection method of the present invention to be described below is a detection method carried out using a nucleic acid sensor obtained by binding luciferase as a labeling substance to the nucleic acid molecule and a labeled carrier, the detection kit of the present invention may include the nucleic acid sensor and a VEGF labeled carrier, for example.

As to the detection reagent and the detection kit of the present invention, reference can be made to the above description regarding the nucleic acid molecule of the present invention, for example. Also, as to the method for using the detection reagent and the detection kit of the present invention, reference can be made to the above description regarding the nucleic acid molecule of the present invention and the following description regarding the detection method of the present invention.

(3) Detection Method

A method for detecting VEGF according to the present invention is a method for detecting VEGF, including the steps of: bringing the nucleic acid molecule of the present invention or the detection reagent of the present invention into contact with a sample to form a complex of VEGF in the sample and the nucleic acid molecule or the detection reagent; and detecting the complex. The detection method of the present invention is characterized in that the nucleic acid molecule or the detection reagent according to the present invention is used therein, and other steps, conditions, or the like are not particularly limited. The detection method of the present invention will be described below with reference to an example where the nucleic acid molecule of the present invention is used in the detection method. It should be noted, however, that, in the following example, the nucleic acid molecule of the present invention is interchangeable with the detection reagent of the present invention.

The nucleic acid molecule of the present invention specifically binds to VEGF. Thus, according to the present invention, VEGF in a sample can be detected specifically by detecting the binding between the VEGF and the nucleic acid molecule or the detection reagent, for example. Specifically, for example, since the amount of the VEGF in the sample can be analyzed, qualitative analysis or quantitative analysis also is possible.

In the present invention, the sample is not particularly limited. The sample is a biological sample, for example. Specific examples of the biological sample include plasma, serum, lymph fluid, whole blood, and tissue culture solutions.

The sample may be a liquid sample or a solid sample, for example. The sample preferably is a liquid sample from the viewpoint of ease of handling, because the liquid sample can be brought into contact with the nucleic acid molecule more easily, for example. In the case of the solid sample, a mixed solution, a liquid extract, a solution, or the like of the solid sample prepared using a solvent may be used, for example. The solvent is not particularly limited, and may be water, physiological saline, or a buffer solution, for example.

In the above-described complex formation step, the method for causing the contact between the sample and the nucleic acid molecule is not particularly limited. The contact between the sample and the nucleic acid molecule preferably is achieved in a liquid, for example. The liquid is not particularly limited, and may be, for example, water, physiological saline, or a buffer solution.

In the complex formation step, the conditions under which the contact between the sample and the nucleic acid molecule is caused are not particularly limited. The contact temperature is, for example, 4° C. to 37° C., preferably 18° C. to 25° C. The contact time is, for example, 10 to 120 minutes, preferably 30 to 60 minutes.

In the complex formation step, the nucleic acid molecule may be an immobilized nucleic acid molecule immobilized on a carrier (solid-phase carrier) or an unimmobilized nucleic acid molecule in a free state, for example. In the latter case, for example, the nucleic acid molecule is brought into contact with the sample in a container. In the former case, the carrier is not particularly limited, and may be a plate, a filter, a column, a substrate, beads, or a container, for example. The container may be a microplate or a tube, for example. The immobilization of the nucleic acid molecule is as described above, for example. In the complex formation step, the sample may be immobilized on a carrier, for example.

The detection step is the step of detecting the binding between the VEGF in the sample and the nucleic acid molecule, as described above. By detecting the presence or absence of the binding between the VEGF and the nucleic acid molecule, it is possible to analyze the presence or absence of the VEGF in the sample (qualitative analysis), for example. Also, by detecting the degree of the binding (the amount of the binding) between the VEGF and the nucleic acid molecule, it is possible to analyze the amount of the VEGF in the sample (quantitative analysis), for example.

The method for detecting the binding between the VEGF and the nucleic acid molecule is not particularly limited. The method may be a conventionally known method for detecting the binding between substances, for example. Specific examples of the method include the above-described SPR.

If binding between VEGF and the nucleic acid molecule is not detected, it is likely that VEGF is not present in the sample. When the binding is detected, it can be determined that the VEGF is present in the sample. Also, by determining the correlation between the concentrations of VEGF and the amounts of the binding beforehand, it becomes possible to analyze the concentration of the VEGF in the sample from the measured amount of the binding on the basis of the correlation.

As an example of the method for detecting the binding between VEGF and the nucleic acid molecule, a detection method carried out using a nucleic acid sensor obtained by binding luciferase as a labeling substance to the nucleic acid molecule and a VEGF labeled carrier will be described below.

First, the nucleic acid sensor is mixed with the sample. When VEGF is present in the sample, the nucleic acid molecule in the nucleic acid sensor binds to the VEGF as a target. On the other hand, when the VEGF is not presence in the sample, the nucleic acid molecule in the nucleic acid sensor remains in a state of being unbound to the target.

Subsequently, the mixture is brought into contact with the VEGF labeled carrier, and then, the VEGF labeled carrier is removed. The carrier may be beads, for example. When the nucleic acid sensor is bound to the VEGF in the mixture, the nucleic acid molecule in the nucleic acid sensor cannot bind to VEGF on the VEGF labeled carrier. Thus, when a substrate for luciferase is added to a fraction from which the VEGF labeled carrier has been removed so as to cause a luminescent reaction, light emission is caused by the catalytic reaction of the luciferase in the nucleic acid sensor. On the other hand, when the nucleic acid sensor in the mixture is in a state of being unbound to VEGF, the nucleic acid molecule in the nucleic acid sensor binds to the VEGF on the VEGF labeled carrier. Accordingly, when the VEGF labeled carrier is removed, the nucleic acid sensor bound to the VEGF labeled carrier is removed together with the VEGF labeled carrier. Thus, when a substrate for luciferase is added to a fraction from which the VEGF labeled carrier has been removed so as to cause a luminescent reaction, light emission caused by the catalytic reaction of the luciferase does not occur because the nucleic acid sensor is not present. Therefore, on the basis of the presence or absence of light emission, it is possible to analyze the presence or absence of the VEGF in the sample (qualitative analysis). Further, the amount of the VEGF in the sample correlates with the amount of the nucleic acid sensor remaining in the fraction after the VEGF labeled carrier has been removed. Therefore, on the basis of the intensity of the light emission, it is possible to analyze the amount of the VEGF in the sample (quantitative analysis).

Second Example Embodiment

The method for producing the nucleic acid molecule according to the present invention is, as described above, a method for producing a nucleic acid molecule that binds to a first biological molecule and does not inhibit a function of the first biological molecule, including the steps of:
(A) bringing a candidate nucleic acid molecule into contact with the first biological molecule to select a nucleic acid molecule that has bound to the first biological molecule as a first selected nucleic acid molecule; and
(B) selecting the first selected nucleic acid molecule as an intended nucleic acid molecule.

The production method of the present invention, for example, further includes, after the step (A), the step of:
(C) bringing a second biological molecule into contact with a complex of the first selected nucleic acid molecule and the first biological molecule to detect a function of the second biological molecule, wherein
after the step (C), in the step (B), the first selected nucleic acid molecule of the complex with which the function of the second biological molecule is detected is selected as an intended nucleic acid molecule.

In the production method of the present invention, the function of the first biological molecule is, for example, a function of binding to the second biological molecule. The function of the first biological molecule is, for example, a function of regulating activity of the second biological molecule by binding to the second biological molecule. The function of regulating activity of the second biological molecule may be, for example, a function of activating or deactivating the second biological molecule. The activation may be, for example, phosphorylation.

In the production method of the present invention, for example, the first biological molecule is a growth factor and the second biological molecule is a receptor. In this case, the production method of the present invention is a method for producing a nucleic acid molecule that binds to a growth factor and does not inhibit a function of the growth factor, including the steps of:
(A) bringing a candidate nucleic acid molecule into contact with the growth factor to select a nucleic acid molecule that has bound to the growth factor as a first selected nucleic acid molecule; and
(B) selecting the first selected nucleic acid molecule as an intended nucleic acid molecule.

In this case, the production method of the present invention, for example, further includes, after the step (A), the step of:
(C) bringing a receptor to which the growth factor binds into contact with a complex of the first selected nucleic acid molecule and the growth factor to detect activation of the receptor, wherein
after the step (C), in the step (B), the first selected nucleic acid molecule of the complex with which the activation of the receptor is detected is selected as an intended nucleic acid molecule.

The production method of the present invention will be described below with reference to an example where the first biological molecule is a growth factor and the second biological molecule is a receptor. It is to be noted, however, that the present invention is not limited to this illustrative example. The combination of the first biological molecule and the second biological molecule is, for example, a combination of a protein and a receptor for the protein. In this case, the combination may be, for example, the combination of proteins in any protein complex. Examples of the combination include the combination of a cytokine and a cytokine receptor and the combination of an enzyme and an enzyme receptor.

In the present invention, the growth factor is a vascular endothelial growth factor (VEGF), cytokine, or a heparin-binding growth factor, for example. In the method for producing the nucleic acid molecule according to the present invention, a commercially available VEGF can be used as VEGF to be brought into contact with a candidate nucleic acid molecule, for example. A specific example of the commercially available VEGF is VEGF165 (PeproTech, Cat: 100-20). In the present invention, VEGF165 also may be referred to simply as "VEGF" hereinafter.

The step (A) is, for example, the step of bringing a candidate nucleic acid molecule into contact with the growth factor to select a nucleic acid molecule that has bound to the growth factor as a first selected nucleic acid molecule.

In the present invention, the expression "binds to a growth factor" (and grammatical variations thereof) also is referred to as "having binding properties to a growth factor" or "binding activity to a growth factor", for example.

The candidate nucleic acid molecule is not particularly limited. For example, a library containing nucleic acids with random sequences can be used.

In the step (A), the method for causing the contact between the candidate nucleic acid molecule and the growth factor is not particularly limited. The contact between the candidate nucleic acid molecule and the growth factor preferably is achieved in a liquid, for example. The liquid is not particularly limited, and may be, for example, water, physiological saline, or a buffer solution. The buffer solution may be a SB1T buffer, for example.

In the step (A), the conditions under which the contact between the candidate nucleic acid molecule and the growth factor is caused are not particularly limited. The contact temperature is, for example, 4° C. to 37° C., preferably 18°

C. to 25° C. The contact time is, for example, 10 to 120 minutes, preferably 30 to 60 minutes.

In the contact between the candidate nucleic acid molecule and the growth factor, the candidate nucleic acid molecule may be an immobilized nucleic acid molecule immobilized on a carrier (solid-phase carrier) or an unimmobilized nucleic acid molecule in a free state, for example. In the latter case, for example, the nucleic acid molecule is brought into contact with the growth factor in a container. In the former case, the carrier is not particularly limited, and may be a plate, a filter, a column, a substrate, beads, or a container, for example. The container may be a microplate or a tube, for example. The immobilization of the candidate nucleic acid molecule is as described above, for example. In the contact between the candidate nucleic acid molecule and the growth factor, the first biological molecule, the second biological molecule, the complex, and a target substance and non-target substance to be described below may be immobilized on a carrier, for example.

In the step (A), the method for detecting the binding between the candidate nucleic acid molecule and the growth factor is not particularly limited. The method may be a conventionally known method for detecting the binding between substances, for example. Specifically, the binding between the candidate nucleic acid molecule and the growth factor can be determined by surface plasmon resonance (SPR) analysis, for example. In the analysis, a BIACORE 3000 (trade name, GE Healthcare UK Ltd.) can be used, for example.

Then, for example, when the binding between the candidate nucleic acid molecule and the growth factor is not detected, it can be determined that the candidate nucleic acid molecule does not bind to the growth factor, and when the binding is detected, it can be determined that the candidate nucleic acid molecule binds to the growth factor.

In the step (A), a nucleic acid molecule that exhibit a dissociation constant against the growth factor (which indicates the binding force to the growth factor) of not more than a few nM can be selected as the first selected nucleic acid molecule, for example.

In the step (A), for example, the candidate nucleic acid molecules may be brought into contact with the growth factor, which is a target substance, and a non-target substance, and among the candidate nucleic acid molecules, a candidate nucleic acid molecule that has bound to the target substance and has not bound to the non-target substance may be selected as the first selected nucleic acid molecules.

In this case, the non-target substance may be, for example, a receptor to which the growth factor binds. The non-target substance may be, for example, a polypeptide including a sequence corresponding to a binding site of the amino acid sequence of a receptor to which the growth factor binds with the growth factor. Thus, the nucleic acid molecule that has not bound to the receptor can be selected as a first selected nucleic acid molecule.

Also, the non-target substance may be, for example, a polypeptide including a sequence corresponding to a binding site of the amino acid sequence of the growth factor with the receptor for the growth factor. Thus, when the growth factor and the nucleic acid molecule are bound, the nucleic acid molecule that does not inhibit the function of the bound growth factor of further binding to the receptor can be selected as the first selected nucleic acid molecule.

When the target substance is an intended growth factor, the non-target substance may be a growth factor other than the intended growth factor, for example. Thus, the nucleic acid molecule that binds to an intended growth factor and does not bind to a growth factor other than the intended growth factor can be selected as the first selected nucleic acid molecule.

Figure 13:
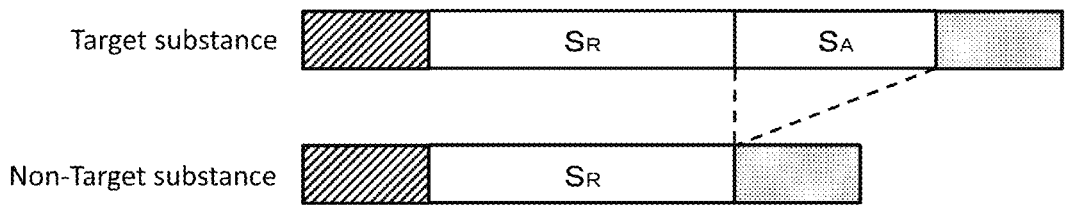
FIG. 13 is a schematic view showing an example of a target substance and an example of a non-target substance in the second example embodiment of the present invention.

As shown in FIG. 13, the target substance may be a polypeptide that includes a sequence ($S_R$) corresponding to a binding site of an amino acid sequence of the growth factor with the receptor for the growth factor and also includes a freely-selected nucleic acid binding sequence ($S_A$) that is different from the sequence corresponding to the binding site with the receptor for the growth factor and the non-target substance may be a polypeptide that includes the sequence ($S_R$) and does not include the nucleic acid binding sequence ($S_A$). For example, the non-target substance may be a polypeptide that includes a sequence in common with the target substance except that it does not include the sequence ($S_A$). In the target substance and the non-target substance, the position and the order of the sequence ($S_R$) and the sequence ($S_A$) are not particularly limited. The target substance and the non-target substance may be, for example, proteins in a splicing variant relationship with each other. In this case, the sequence ($S_A$) may be, for example, an amino acid sequence encoded by a freely-selected exon. The sequence ($S_A$) may be, for example, a sequence that includes a heparin binding domain (HBD) to be described below. Thus, the nucleic acid molecule that binds to the sequence ($S_A$) and does not bind to the sequence ($S_R$) in an intended growth factor can be selected as the first selected nucleic acid molecule.

When the intended growth factor is, for example, a growth factor having a sequence including HBD to be described below, the growth factor other than the intended growth factor is, for example, a growth factor having a sequence not including HBD. The growth factor having a sequence including HBD is, for example, VEGF165, and the growth factor having a sequence not including HBD is, for example, VEGF121 to be described below.

When the target substance is, for example, VEGF165, the non-target substance is, for example, a receptor to which the VEGF165 binds. Examples of the receptor to which the VEGF165 binds include VEGFR-1 (FLT-1) and VEGFR-2 (KDR/FLK-1). Examples of a polypeptide including a sequence corresponding to a binding site of the amino acid sequence of VEGFR-1 with VEGF165 include a second Ig-like domain (aa:129-229) represented by the following SEQ ID NO: 8. Examples of a polypeptide including a sequence corresponding to a binding site of the amino acid sequence of VEGFR-2 with VEGF165 include a second Ig-like domain (aa:141-207) represented by the following SEQ ID NO: 9 and a third Ig-like domain (aa:224-320) represented by the following SEQ ID NO: 10. Examples of a polypeptide including a sequence corresponding to a binding site of the amino acid sequence of VEGF165 with VEGFR-1 include exon 3 represented by the following SEQ ID NO: 11. Examples of a polypeptide including a sequence corresponding to a binding site of the amino acid sequence of VEGF165 with VEGFR-2 include exon 4 represented by the following SEQ ID NO: 12.

```
Second Ig-like domain
                                              (SEQ ID NO: 8)
SDTGRPFVEMYSE1PEIIHMTEGRELVIPCRVTSPNITVTLKKFPLDTLI

PDGKRIIWDSRKGFIISNATYKEIGLLTCEATVNGHLYKTNYLTHRQTNT

I

Second Ig-like domain
                                              (SEQ ID NO: 9)
NKNKTVV1PCLGSISNLNVSLCARYPEKRFVPDGNRISWDSKKGFTIPSY

MISYAGMVFCEAKINDE

Third Ig-like domain
                                              (SEQ ID NO: 10)
DVVLSPSHGIELSVGEKLVLNCTARTELNVGIDFNWEYPSSKHQHKKLVN

RDLKTQSGSEMKKFLSTLTIDGVTRSDQGLYTCAASSGLMTKKNST

Exon 3
                                              (SEQ ID NO: 11)
VKFMDVYQRSYCHPIETLVDIFQEYPDEIEYIFKPSCVPLMRCGGCCNDE

GLECVPTEESNITMQ

Exon 4
                                              (SEQ ID NO: 12)
IMRIKPHQGQHIGEMSFLQHNKCECR
```

The step (C) is, for example, the step of bringing the receptor to which the growth factor binds into contact with a complex of the first selected nucleic acid molecule and the growth factor to detect the activation of the receptor.

In the step (C), for example, a commercially available VEGF receptor can be used as the receptor to be brought into contact with the complex of the first selected nucleic acid molecule and the VEGF. A specific example of the commercially available VEGF receptor is a VEGF receptor (R&D systems, Cat. No: 357-KD-050/CF).

In the step (C), the method for causing the contact between the complex of the first selected nucleic acid molecule and the growth factor and the receptor to which the growth factor binds or the conditions under which the contact between them is caused are not particularly limited, for example, and they are the same as the contact method and the contact conditions for the candidate nucleic acid molecule and the growth factor in the step (A).

In the step (C), the method for detecting the activation of the receptor to which the growth factor binds is not particularly limited. The detection can be performed by, for example, measuring the phosphorylation of the receptor to which the growth factor binds. Specifically, the detection can be performed by ELISA or Western blotting, for example.

Then, for example, when activation of the receptor to which the growth factor binds is not detected, it can be determined that the complex does not activate the receptor, and when the activation is detected, it can be determined that the complex activates the receptor.

In the step (C), activation of the receptor to which the growth factor binds may be detected indirectly by, for example, detecting the binding between the complex of the first selected nucleic acid molecule and the growth factor and the receptor to which the growth factor binds.

The method for detecting the binding is not particularly limited. For example, the detection can be performed by SPR, capillary electrophoresis, or Native-PAGE.

The above description uses the growth factor VEGF to illustrate the method. It will be recognized by a person skilled in the art that the method can be applied to other proteins. Additional non-limiting examples include:

Other growth factors with a heparin binding domain such as
- Long (heparin-binding) and short (non-heparin binging) isoforms of PDGF-A generated by alternative splicing (UNIPROT accession numbers P04085-1 and P04085-2), and
- Four splice variants of P1GF containing alternative and truncated forms of heparin-binding domains (UNIPROT accession numbers P49763-1, P49763-2, P49763-3, P49763-4);

Other cytokines with a heparin binding domain such as
- Interferon gamma (IFN gamma) containing unstructured C-terminal heparin-binding domain (UNIPROT accession number P01579-1),
- Human TNF-alfa (heparin-binding) and its N-terminally truncated version lacking ability to bind heparin (Kenig, M. et al. 2008. Journal of Chromatography B, 867, pp. 119-125), and
- IL-12, where heparin-binding is attributed to an independently folding C-terminal domain of the p40 subunit that can be removed by molecular cloning (Gamier, P. et al. 2018. Cytokine 110, pp 159-168);

Growth factors engineered to include a heparin binding domain such as
- a recombinant construct including a short isoform of PDGF-A and a C-terminal HBD from IFN gamma;

Cytokines engineered to include a heparin binding domain such as
- a recombinant construct including IL-1 and a HBD from a long isoform PDGF-A, and
- a recombinant construct including IL-2 and a HBD from a cell surface Hep/HS-interacting protein (Liu, S., 1997. Proc. Natl. Acad. Sci. USA 94, pp. 1739-1744);

Other secreted proteins with a heparin binding domain such as
- Heparin/Heparan Sulfate (HP/HS) Interacting Protein (Liu et al. 1997. The Journal of Biological Chemistry 272, pp. 25856-25862; Liu, S., 1997. Proc. Natl. Acad. Sci. USA 94, pp. 1739-1744);

Other secreted proteins with an engineered heparin binding domain;

Proteins (including growth factors, cytokines, and secreted proteins) that include a domain that is separately targetable from the domain having the desired biological function, such as
- Four isoforms of human IGF-1 generated by alternative splicing that contain distinct variants of the C-terminal E-peptide that can be proteolytically removed without loss of receptor binding (UNIPROT accession numbers P05019-1, P05019-2, P05019-3, P05019-4), and
- Four isoforms of human FGF-2 generated by alternative initiation and bearing distinct N-terminal domains that do not interfere with receptor binding (UNIPROT accession numbers P09038-1, P09038-2, P09038-3, P09038-4); and Proteins (including growth factors, cytokines, and secreted proteins) that are engineered to include a domain (e.g. albumin, FC SUMO, GSO, or other domains that are well known to those skilled in the art) that is separately targetable from the domain having the desired biological function.

The step (B) is the step of selecting the first selected nucleic acid molecule as an intended nucleic acid molecule.

According to the method for producing a nucleic acid molecule according to the present invention, it is possible to obtain a nucleic acid molecule that binds to a first biological molecule and does not inhibit the function of the first biological molecule.

Third Example Embodiment (1) Biomaterial

The biomaterial according to the present invention includes, as described above, a binding nucleic acid molecule; and a carrier, the binding nucleic acid molecule being bound to the carrier, wherein the binding nucleic acid molecule binds to a predetermined protein and does not inhibit a function of the predetermined protein.

The carrier is, for example, a polymer. Examples of the polymer include gels and particles. An example of a polymer carrier is a poly(ethylene glycol)-based gel created with a photo-initiated chemistry. Specifically, a monomer solution is prepared in an aqueous buffer containing 10% wt/vol 4600MW poly(ethylene glycol)-diacrylate (PEGDA), 0.05% photoinitiator Irgacure-2959 (12959), and a binding nucleic acid that has been functionalized with a free thiol or acrylate moiety. Polymerization of the gel is accomplished by shining a 100WHg short-arc lamp (Omnicure® 1000, EXFO, Mississaugua, Ont., Canada) with the manufacturer-supplied filter for 365 nm exposure on the sample for 10 minutes. During the polymerization reaction, the binding nucleic acid will become covalently incorporated into the polymer. In this system, the presence of ester bonds within each PEGDA monomer makes the resulting polymer susceptible to hydrolytic degradation. However, the rate of degradation would be generally considered too slow for tissue engineering applications. Thus, for the sake of this disclosure, PEGDA hydrogels are considered non-degradable.

The polymer carrier can also be formulated to be hydrolytically degradable. An example of a hydrolytically degradable polymer carrier is a caprolatone-based gel created with a photo-initiated chemistry. Specifically, a monomer solution is prepared in an aqueous buffer containing 6% wt/vol methacrylated hyaluronic acid (MeHA) and methacrylated caprolactone HA (MeCLHA) at a 1:1 ratio, 0.05% photoinitiator Irgacure-2959 (12959), and a binding nucleic acid that has been functionalized with a free thiol or acrylate moiety. Polymerization of the gel is accomplished by shining a 100WHg short-arc lamp (Omnicure® 1000, EXFO, Mississaugua, Ont., Canada) with the manufacturer-supplied filter for 365 nm exposure on the sample for 10 minutes. In this system, the presence of caprolactone linkages makes the polymer system susceptible to hydrolytic degradation at a rate that is significantly faster than the PEGDA-based polymers described in the previous section.

The polymer carrier can also be formulated to be enzymatically degradable. An example of an enzymatically degradable polymer carrier is a poly(ethylene glycol)-based gel created with thiol-ene photo-initiated chemistry. Specifically, a monomer solution is prepared in an aqueous buffer containing 6% wt/vol 20K 4-arm poly(ethylene glycol)-norbornene (PEG-NB), 6 mM di-cysteine enzymatically degradable crosslinker peptide (KCGPQGIAGQCK; SEQ ID NO: 14), 0.01% photoinitiator lithium phenyl-2,4,6-trimethylbenzoylphosphinate (LAP), and a binding nucleic acid that has been functionalized with a free thiol or norbornene moiety. In this system, cysteine-containing peptides, 4-arm PEG-NB monomers, and the functionalized binding nucleic acid are mixed in a 1:1 stoichiometric ratio with respect to "thiol" and "ene" functional groups. In the presence of the LAP photoinitiator, and upon exposure 385 nm light, the thiol group is added to the norbornene, forming a norbornene-thioether linkage. Polymerization of the hydrogels is accomplished by shining a handheld LED flashlight emitting 385 nm light over the solution for 1 minute. In this system, crosslinking peptides require the presences of at least two cystienes (R-groups contain "thiol" moieties), allowing them to covalently react with more than one multi-armed "ene"-functionalized PEG. A 4-arm PEG-NB is reacted with a dicysteine peptide crosslinker that is designed to be susceptible to enzymatic degradation by naturally occurring extracellular matrix remodeling enzymes. Specifically, a collagen-based sequence, KCGPQG*IAGQCK (SEQ ID NO: 14), is used for its known susceptibility to cleavage by matrix metaloproteinases (MMPs), where the "*" denotes the site of enzymatic cleavage.

The polymer carrier systems described in this document are provided as examples only and are chosen to illustrate how specific compositional elements can be incorporated into the polymer matrix to impart specific properties to the material carrier. In these examples, distinct degradation properties of the material carrier would be achieved. It is understood that carriers for a binding nucleic acid can be designed to incorporate other mechanisms of degradation, alone or in combination, to create a wide range of materials with distinct degradation profiles.

Materials containing substrates for cellular adhesion and migration can be used to create nucleic acid carriers that also provide a scaffolding function for cells and tissues. The incorporation of polypeptides (e.g. CRGD), full-length proteins (e.g. fibrinogen, collagen, laminin, etc.), or protein fragments thereof, that present binding sites for cell attachment can be used in combination with a binding nucleic acid to create material carriers with additional functionality for biological applications.

Molecular components used to create carriers for a binding nucleic acid are not limited to poly(ethylene glycol)-diacrylate (PEGDA), methacrylated hyaluronic acid (MeHA), methacrylated caprolactone HA (MeCLHA), and poly(ethylene glycol)-norbornene (PEG-NB) as presented in the examples. Those skilled in the art would understand that a plurality of molecular components can be employed to create material carriers for binding nucleic acids.

Chemistries and reactable groups used to create carriers for a binding nucleic acid are not limited to the photo-initiated chemistries presented in the examples. Those skilled in the art would understand that a plurality of reaction mechanisms utilizing a plurality of reactable chemical functional groups can be employed to create material carriers for binding nucleic acids.

The method for binding the binding nucleic acid molecule to the carrier is not particularly limited and can be performed by a known method. The binding nucleic acid molecule can be caused to bind to the carrier via an additional sequence.

The binding nucleic acid molecule is not particularly limited as long as it binds to a predetermined protein and does not inhibit a function of the predetermined protein. The function of the predetermined protein is, for example, a function of binding to a receptor for the protein. Also, the function of the predetermined protein is, for example, a function of regulating activity of the receptor by binding to the receptor. The function of regulating activity of the receptor may be, for example, a function of activating or deactivating the receptor. The activation may be, for example, phosphorylation. The nucleic acid molecule produced by the method for producing a nucleic acid molecule according to the present invention can be used as the binding nucleic acid molecule, for example.

The predetermined protein is, for example, a growth factor. The growth factor may be, for example, VEGF. When the growth factor is VEGF, the nucleic acid molecule that binds to VEGF of the present invention can be used as the binding nucleic acid molecule, for example.

The binding nucleic acid molecule may be contained in the biomaterial as a conjugate bound to the predetermined protein or in a state of being unbound to the predetermined protein, for example. In the latter case, for example, by disposing the biomaterial in a living organism, the binding nucleic acid molecule can bind to the predetermined protein in the living organism.

According to the biomaterial of the present invention, for example, by bringing the biomaterial of the present invention into contact with a living organism, it is possible to exhibit the function of the predetermined protein bound to the binding nucleic acid molecule on the living organism. Examples of the living organism include humans and non-human animals, and examples of the non-human animal include mammals such as monkey, dog, rabbit, cow, horse and the like. The contact is not particularly limited. For example, the biomaterial may be disposed in the living organism or may be taken by the living organism. The site of the living organism in which the biomaterial is disposed may be any site where it is required to exhibit the function of the predetermined protein, and is not particularly limited, and is, for example, the skin.

The usage form of the biomaterial of the present invention will be described below in detail. As a first example, the biomaterial of the present invention is a biological scaffold, and the biological scaffold includes the binding nucleic acid molecule of the present invention bound to VEGF and a biodegradable gel bound to the binding nucleic acid molecule. When the biological scaffold is disposed at a wound site of the living organism, the VEGF bound to the binding nucleic acid molecule binds to the VEGF receptor at the wound site to activate the VEGF receptor. This can, for example, promote healing of the wound site.

As a second example, the biomaterial of the present invention is an oral medicine, and the oral medicine includes the binding nucleic acid molecule bound to the predetermined protein and biodegradable particles bound to the binding nucleic acid molecule. When the oral medicine is taken by the living organism, the biodegradable particles are decomposed in the living organism to release the predetermined protein bound to the binding nucleic acid molecule, thereby exhibiting the function of the predetermined protein. Thus, for example, the timing or the like of exhibiting the function of the predetermined protein in the living organism can be regulated.

As described above, according to the biomaterial of the present invention, for example, the function of the predetermined protein can be exhibited on the living organism at a freely-selected position and at a freely-selected timing.

The biomaterial of the present invention can be used, for example, in a treatment method of a living organism. The treatment method of a living organism includes, for example, a step of bringing the biomaterial of the present invention into contact with a living organism. The contact is, for example, as described above.

(2) Production Method for Biomaterial

The method for producing a biomaterial of the present invention includes the step of binding a binding nucleic acid molecule to a carrier, wherein the binding nucleic acid molecule binds to a predetermined protein and does not inhibit a function of the predetermined protein. The carrier, the binding nucleic acid molecule, and the predetermined protein are, for example, as described above.

The step of binding the binding nucleic acid molecule to the carrier may include, for example, the steps of adding an additional sequence to the carrier and binding the binding nucleic acid molecule to the additional sequence. These steps can be performed, for example, using a known method. Thereby, the binding nucleic acid molecule can caused to bind to the carrier via an additional sequence.

The method for producing a biomaterial of the present invention may further include, for example, the step of binding the predetermined protein to the binding nucleic acid molecule. The step of binding the predetermined protein to the binding nucleic acid molecule is not particularly limited, and the binding nucleic acid molecule can be brought into contact with the predetermined protein by a known method.

EXAMPLES

Next, examples of the present invention will be described. It is to be noted, however, that the present invention is not limited by the following examples by any means. Commercially available reagents in the examples were used in accordance with their protocols, unless otherwise stated.

Example 1

The present example examined the binding properties of aptamers of the present invention to VEGF by SPR analysis.

(1) Aptamers

As aptamers of Example 1, aptamers 1 to 5 consisting of the following polynucleotides were synthesized. The aptamers 2 to 4 were aptamers obtained by truncating the aptamer 1. The aptamer 5 is a polynucleotide consisting of a base sequence having 89.5% identity to the base sequence of the aptamer 1.

```
Aptamer 1: VEGF746CaP_R8m1
                                        (SEQ ID NO: 1)
GGATTGCCCGATTCACCGTAAACAGTTCTGGTTCCTTAGTTTAAAGTCAC

GTCTTAGTTTAAGGCATTCTGGAGCGGCATAAC

Aptamer 2: VEGF746CaP_5s31
                                        (SEQ ID NO: 2)
CCTTAGTTTAAAGTCACGTCTTAGTTTAAGG Aptamer 3: VEGF746CaP_5s49
                                        (SEQ ID NO: 3)
CCGTAAACAGTTCTGGTTCCTTAGTTTAAAGTCACGTCTTAGTTTAAGG Aptamer 4: VEGF746CaP_5s62
                                        (SEQ ID NO: 4)
TTCACCGTAAACAGTTCTGGTTCCTTAGTTTAAAGTCACGTCTTAGTTTA

AGGCATTCTGGA

Aptamer 5: VEGF746CaP_R8m49
                                        (SEQ ID NO: 7)
GGATTGCCCGATTCACCGTAAACAGTTCTTACATTAGTTTAAAGTCACGTC

TTAGTTTAATTAAGCATTCTGGAGCGGCATAAC
```

The predicted secondary structures of the aptamers 1 to 5 are shown in FIGS. 1A to 1E, respectively. It is to be noted, however, that the predicted secondary structures are not limited thereto.

To the 3' end of each of the aptamers, 20-mer polydeoxyadenine (poly(dA)) was added. The thus-obtained poly(dA)-added aptamers were used in SPR to be described below.

(2) Sample

Figure 2:
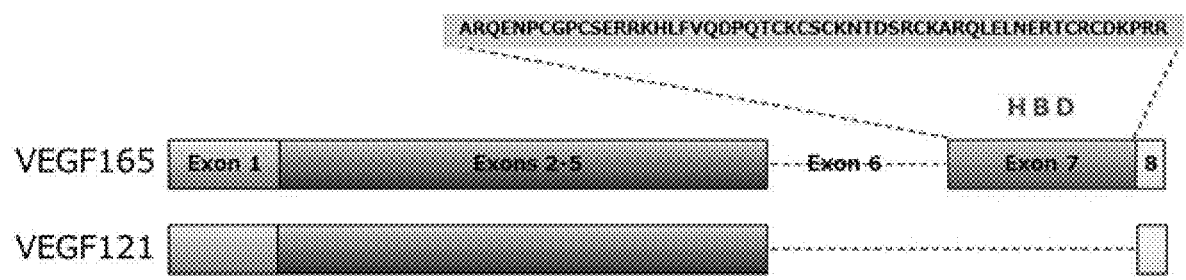
FIG. 2 is a schematic view of two mRNA splice variants which encode different isoforms of VEGF. The amino acid sequence of the heparin binding domain encoded by exon 7 is depicted (SEQ ID NO: 13).

A VEGF sample was prepared using VEGF165 in the following manner. As shown in FIG. 2, VEGF165 does not contain the amino acids encoded by exon 6, but does contain the amino acids encoded by exon 7 (the HBD), represented by the following SEQ ID NO: 13.

HBD (SEQ ID NO: 13)
ARQENPCGPCSERRKHLFVQDPQTCKCSCKNTDSRCKARQLELNERTCRC

DKPRR

VEGF165 (PeproTech, Cat: 100-20) was dissolved at a concentration of 1 mg/mL in distilled water that had been sterilized. The resultant solution was used as a VEGF sample. In the analysis of the binding properties etc. to be described below, an SB1T buffer was used to dilute the VEGF sample. The composition of the SB1T buffer was as follows: 40 mmol/L HEPES, 125 mmol/L NaCl, 5 mmol/L KCl, 1 mmol/L $MgCl_2$, and 0.05% Tween® 20. The pH of the SB1T buffer was 7.5.

As control 1, a sample was prepared in the same manner, except that VEGF121 (PeproTech, Cat: 100-20A) was used instead of the VEGF165. As shown in FIG. 2, the amino acid sequence of VEGF121 corresponds to the amino acid sequence of VEGF in which the nucleotides encoding exon 6 and exon 7 are deleted. Further, as control 2, a sample was prepared in the same manner, except that BSA (Sigma, Cat. No: #A7906) was used instead of the VEGF165.

(3) Analysis of Binding Properties by SPR

The analysis of the binding properties was carried out using a ProteOn XPR36 (BioRad) in accordance with its instructions for use.

First, as a sensor chip designed specifically for the ProteOn, a streptavidin-immobilized chip (trade name: ProteOn NLC Sensor Chip, BioRad) was set in the ProteOn XPR36. 5 μmol/L biotinylated poly(dT) was injected to a flow cell of the sensor chip using ultrapure water (DDW), and the binding was allowed to proceed until the signal intensity (RU: Resonance Unit) was saturated. The biotinylated poly (dT) was prepared by biotinylating the 5' end of 20-mer deoxythymidine. Then, each of the poly(dA)-added aptamers (200 nmol/L) was injected to the flow cell of the chip using an SB1T buffer at a flow rate of 25 μL/min for 80 seconds, and the binding was allowed to proceed until the signal intensity was saturated. Subsequently, each of the samples (5 nmol/L) was injected using an SB1T buffer at a flow rate of 50 μL/min for 300 seconds, followed by washing performed by flowing the SB1T buffer under the same conditions. With the time at which the injection was started being 0 seconds, the signal intensity after the sample injection was measured. The SPR was carried out at 25° C.

Figure 3A:
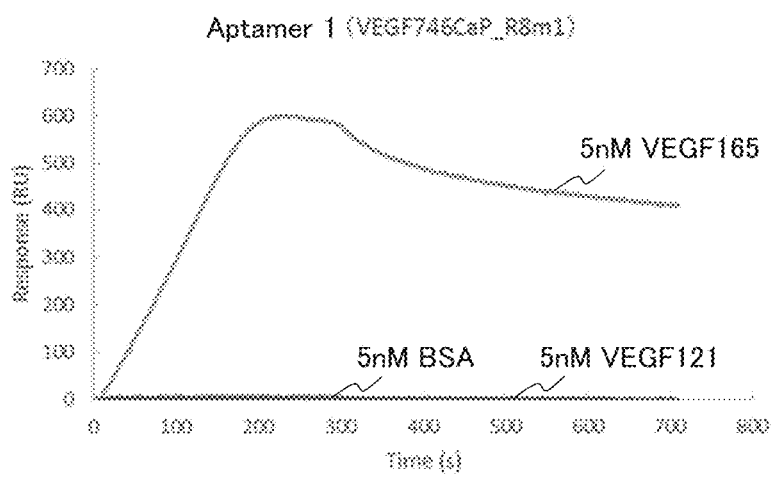
FIGS. 3A to 3E are graphs respectively showing the binding properties of the aptamers 1 to 5 to VEGF165 in Example 1 of the present invention.
Figure 3B:
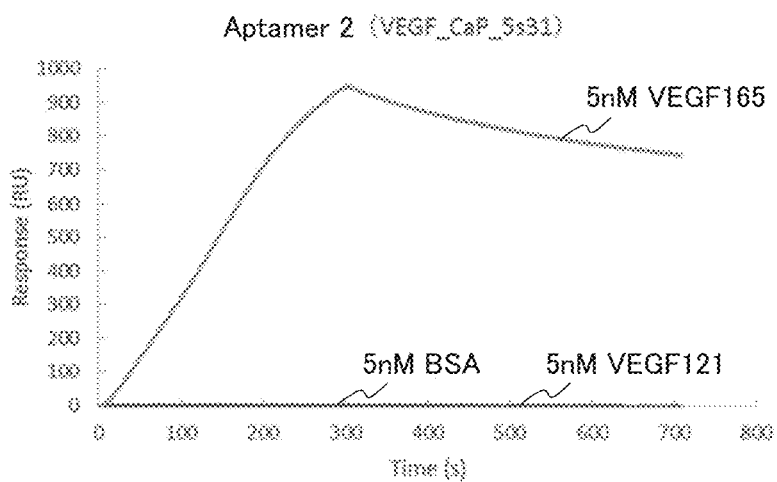
Figure 3C:
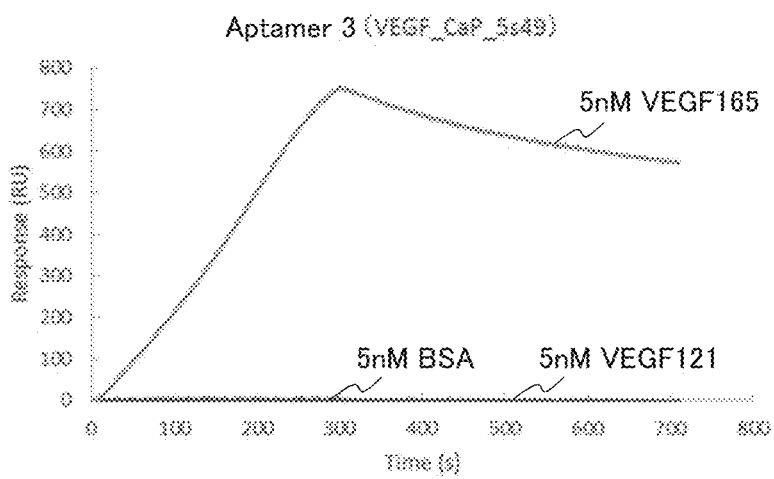
Figure 3D:
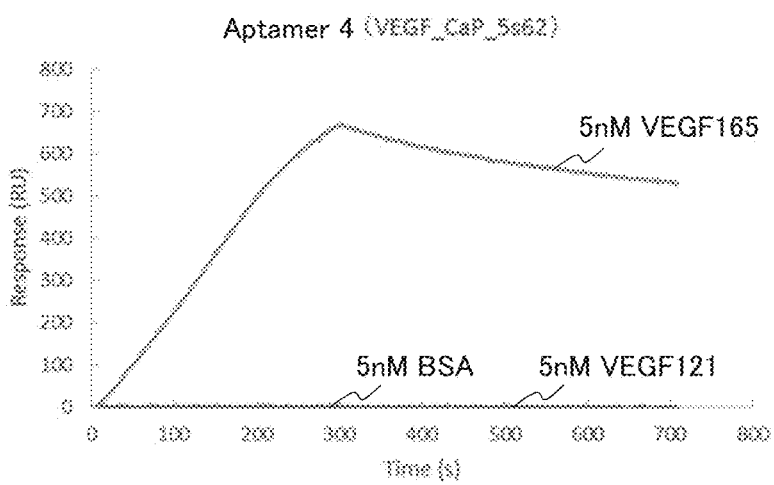
Figure 3E:
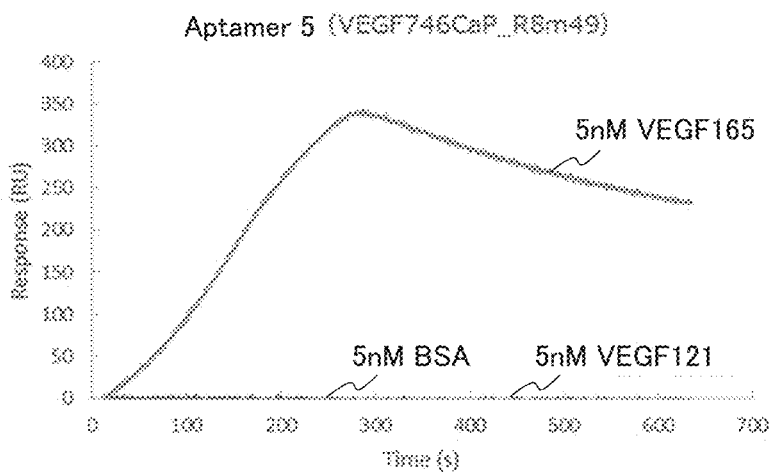

The results obtained are shown in FIGS. 3A to 3E. FIGS. 3A to 3E are graphs respectively showing the binding properties of the aptamers 1 to 5 to 5 nmol/L VEGF165. FIG. 3A shows the result obtained regarding the aptamer 1 (VEGF746CaP_R8m1). FIG. 3B shows the result obtained regarding the aptamer 2 (VEGF746CaP_5s31). FIG. 3C shows the result obtained regarding the aptamer 3 (VEGF746CaP_5s49). FIG. 3D shows the result obtained regarding the aptamer 4 (VEGF746CaP_5s62). FIG. 3E shows the result obtained regarding the aptamer 5 (VEGF746CaP_R8m49). The horizontal axis indicates the time (sec) elapsed after the start of the sample injection, and the vertical axis indicates the signal intensity (RU). As can be seen in FIGS. 3A to 3E, the aptamers 1 to 5 exhibited binding properties to the VEGF165. In contrast, in control 1 (VEGF121) and control 2 (BSA), the aptamers 1 to 5 all exhibited a signal intensity of 0 or less, and they all exhibited no binding properties. These results demonstrate that the aptamers 1 to 5 bind to VEGF165 with high specificity, and the binding can be detected by measuring the signal intensity.

As described above, VEGF165 includes exon 7 (HBD) in the amino acid sequence of VEGF, whereas HBD is deleted in VEGF121. Accordingly, it is considered that the aptamers 1 to 5 bind to exon 7 (HBD) in the amino acid sequence of VEGF. Also, it is considered that the aptamers 1 to 5 can bind not only to VEGF165 but also to, for example, proteins, cytokines, and growth factors having the amino acid sequence corresponding to the HBD. It is to be noted, however, that these considerations are based on speculation, and the present invention is not limited or restricted by this speculation.

Example 2

The present example examined the binding properties of the aptamers of the present invention to VEGF in the absence of calcium ions and in the presence of calcium ions.

First, the binding properties of the aptamers to VEGF in the absence of calcium ions were analyzed using the VEGF sample in the same manner as in Example 1, except that the concentration of the VEGF165 in the sample was set to: 0.8, 1.0, 1.2, 1.6, or 2 nmol/L for the aptamer 1; 0.1, 0.2, 0.4, or 0.6 nmol/L for the aptamers 2, 3, and 4; and 0.2, 0.4, 0.6, and 0.8 nmol/L for the aptamer 5.

Figure 4A:
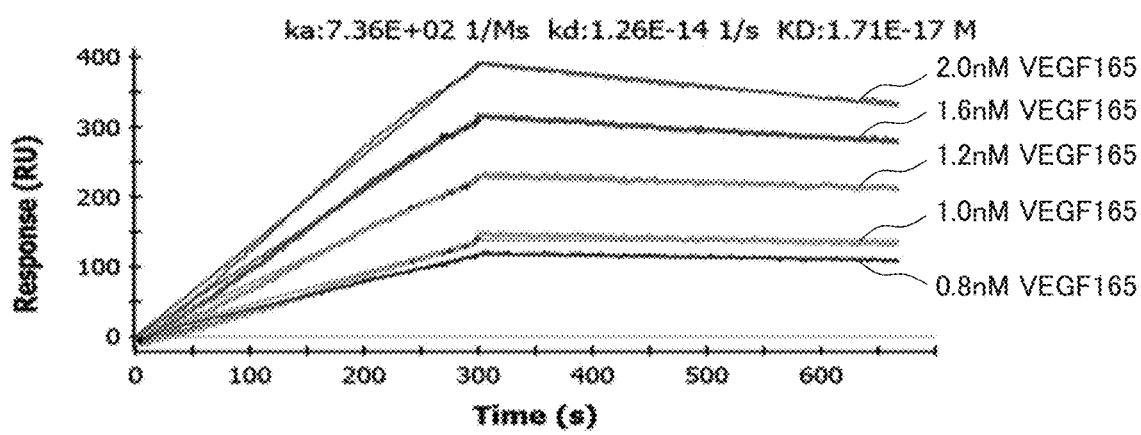
FIGS. 4A to 4E are graphs respectively showing the binding properties of the aptamers 1 to 5 to VEGF165 in Example 2 of the present invention.
Figure 4B:
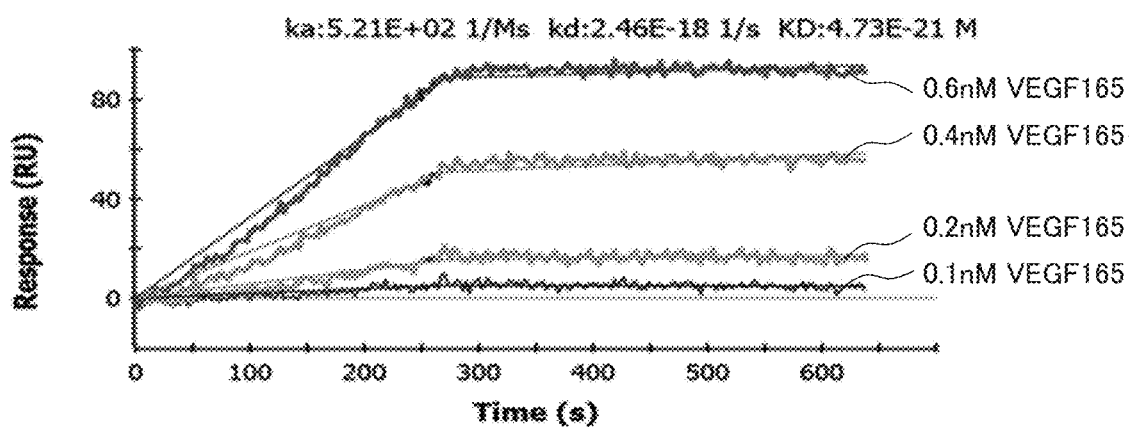
Figure 4C:
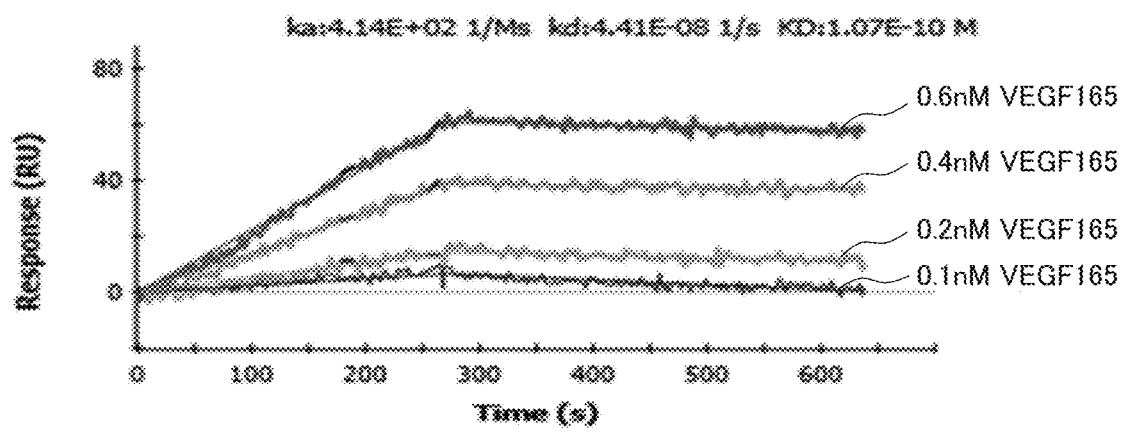
Figure 4D:
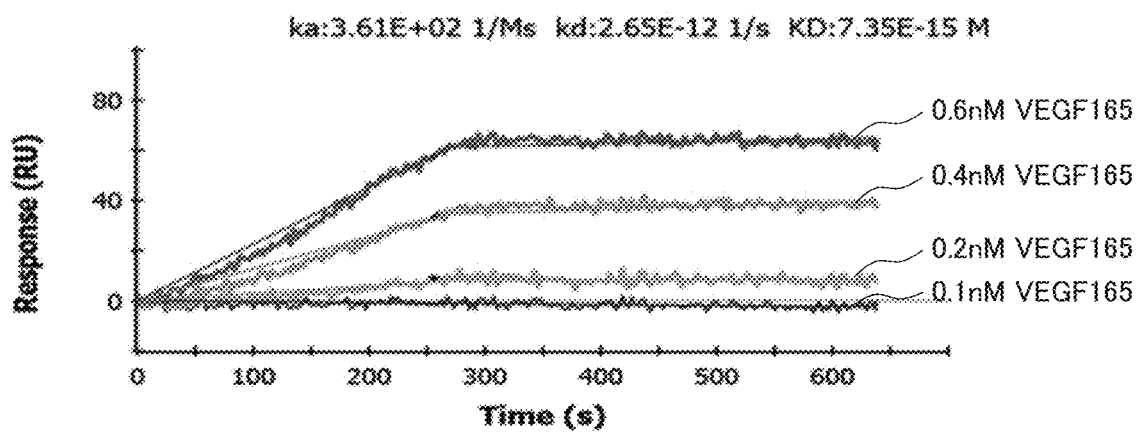
Figure 4E:
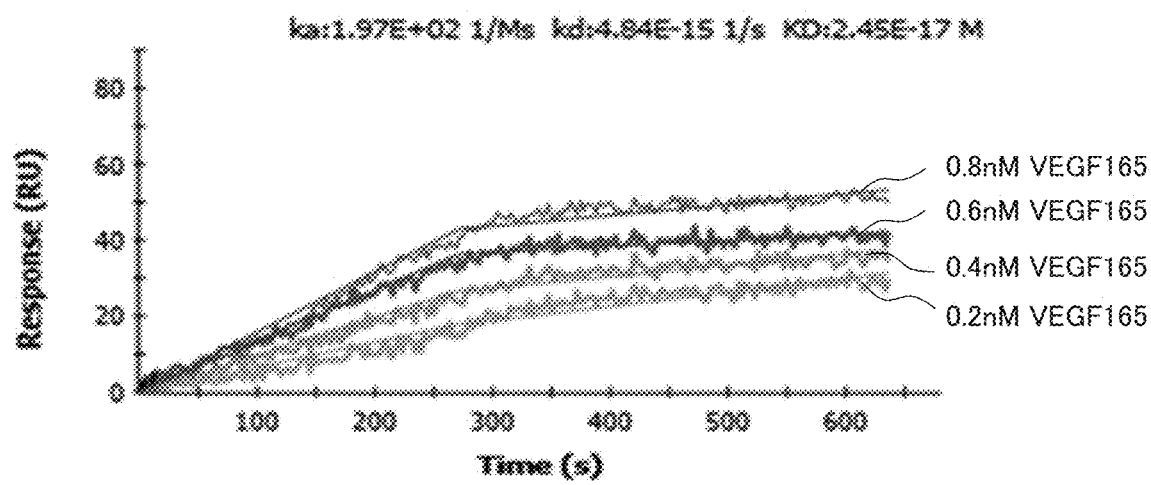

The results obtained are shown in FIGS. 4A to 4E. FIGS. 4A to 4E are graphs respectively showing the binding properties of the aptamers 1 to 5 to the VEGF165 in the absence of calcium ions. FIG. 4A shows the result obtained regarding the aptamer 1 (VEGF746CaP_R8m1). FIG. 4B shows the result obtained regarding the aptamer 2 (VEGF746CaP_5s31). FIG. 4C shows the result obtained regarding the aptamer 3 (VEGF746CaP_5 s49). FIG. 4D shows the result obtained regarding the aptamer 4 (VEGF746CaP_5 s62). FIG. 4E shows the result obtained regarding the aptamer 5 (VEGF746CaP_R8m49). The horizontal axis indicates the time (sec) elapsed after the start of the sample injection, and the vertical axis indicates the signal intensity (RU). As can be seen in FIGS. 4A to 4E, the aptamers 1 to 5 all exhibited binding properties to the VEGF165. Further, the signal intensities exhibited by the aptamers 1 to 5 increased as the concentration of the VEGF165 became higher. These results demonstrate that the concentration of VEGF165 in a sample can be analyzed quantitatively by measuring the signal intensity using the aptamers 1 to 5 of the present invention.

Further, from the results of the SPR analysis shown in FIGS. 4A to 4E, the kinetic parameter was calculated. As a result, it was found that the dissociation constants (KD) of the aptamers 1 to 5 against the VEGF165 in the absence of calcium ions were $1.71 \times 10^{-17}$, $4.73 \times 10^{-21}$, $1.07 \times 10^{-10}$, $7.35 \times 10^{-15}$, and $2.45 \times 10^{-17}$ mol/L, respectively, and the aptamers 1 to 5 all exhibited excellent binding properties. Also, it was found that the aptamer 2, which is the truncated aptamer of the aptamer 1, exhibited a higher binding force to the VEGF165 than the aptamer 1.

Next, the binding properties of the aptamers to VEGF in the presence of calcium ions were analyzed using the VEGF sample in the same manner as in Example 1, except that the concentration of the VEGF165 in the sample was set to 0.1, 0.2, 0.4, or 0.6 nmol/L for the aptamers 1 to 4 and 0.2, 0.4, 0.6, and 0.8 nmol/L for the aptamer 5 and an SB1T buffer (Ca$^{2+}$) was used instead of the SB1T buffer. The composition of the SB1T buffer (Ca$^{2+}$) was as follows: 40 mmol/L HEPES, 125 mmol/L NaCl, 5 mmol/L KCl, 1 mmol/L MgCl$_2$, 1 mmol/L CaCl$_2$, and 0.05% Tween® 20. The pH of the SB1T buffer (Ca$^{2+}$) was 7.5.

Figure 5A:
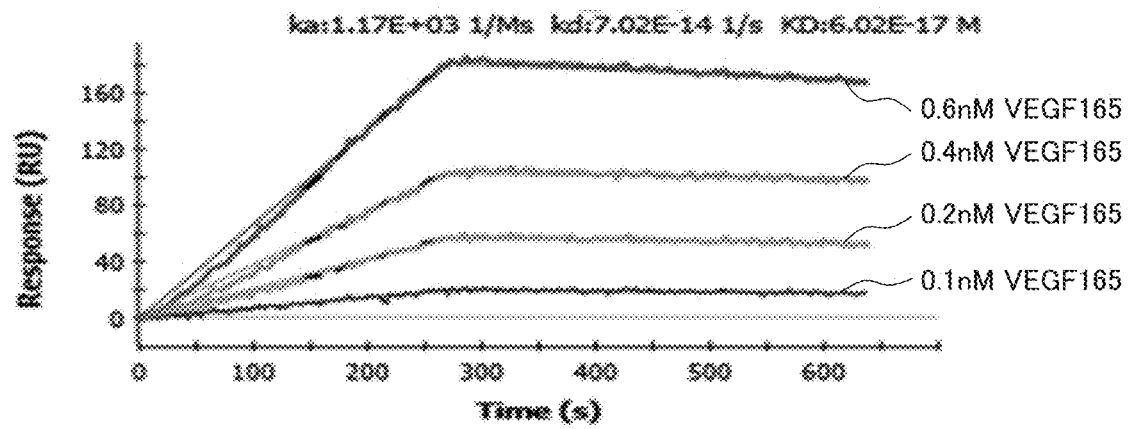
FIGS. 5A to 5E are graphs respectively showing the binding properties of the aptamers 1 to 5 to VEGF165 in the presence of calcium ions in Example 2 of the present invention.
Figure 5B:
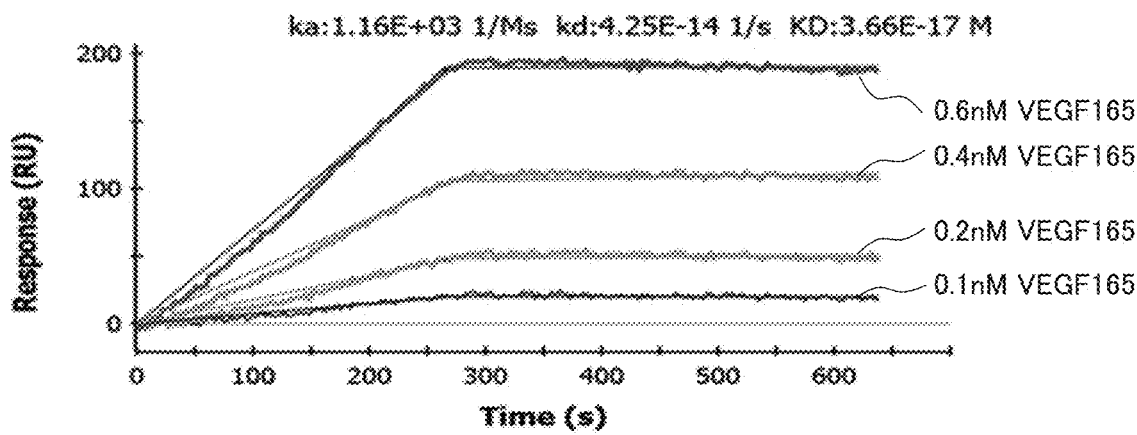
Figure 5C:
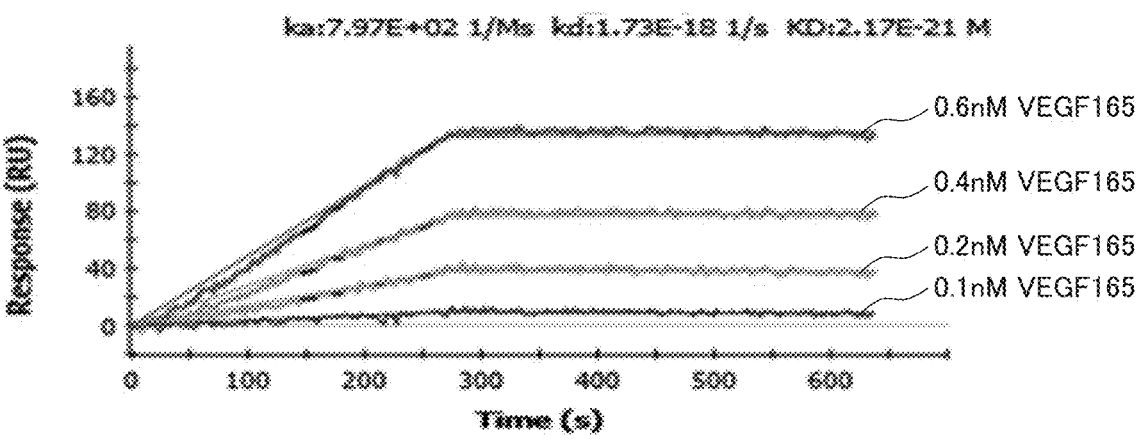
Figure 5D:
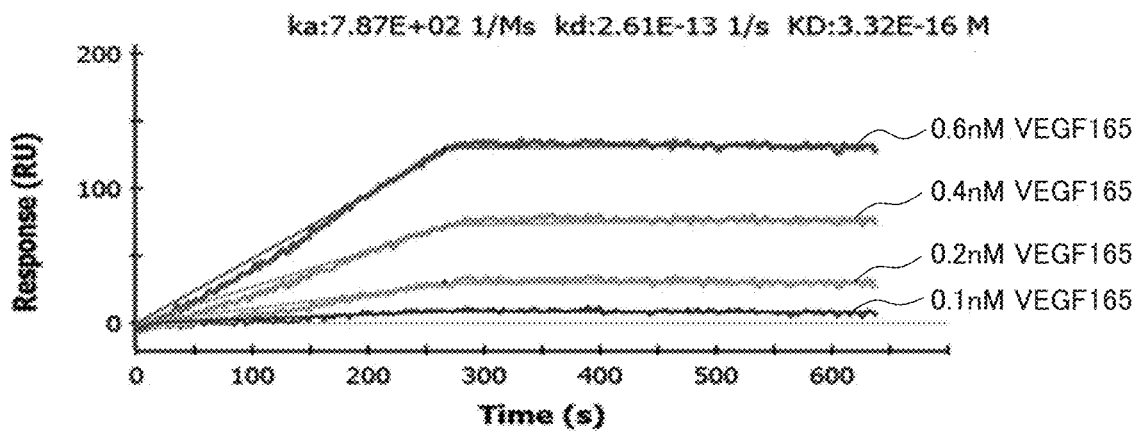
Figure 5E:
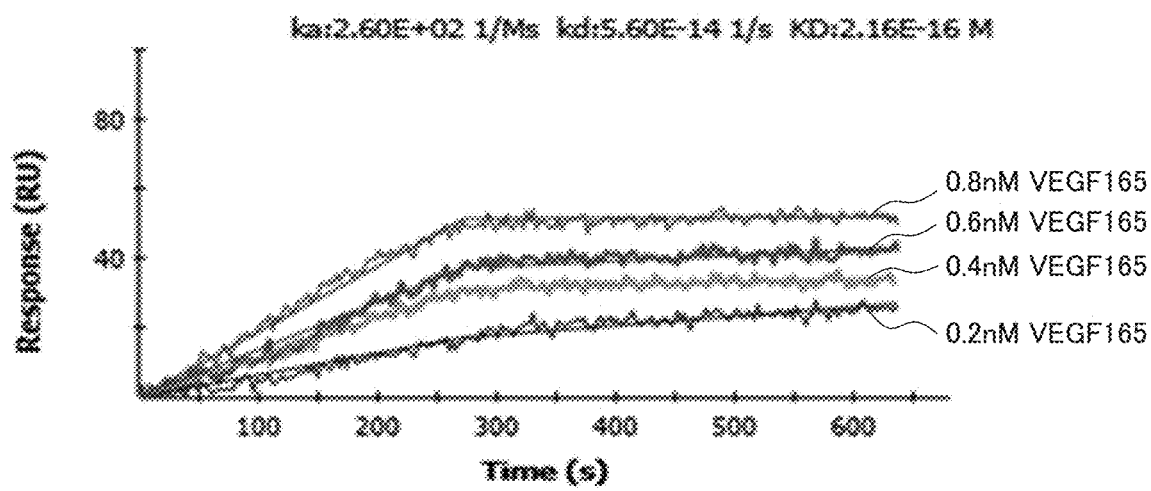

The results obtained are shown in FIGS. 5A to 5E. FIGS. 5A to 5E are graphs respectively showing the binding properties of the aptamers 1 to 5 to the VEGF165 in the presence of calcium ions. FIG. 5A shows the result obtained regarding the aptamer 1 (VEGF746CaP_R8m1). FIG. 5B shows the result obtained regarding the aptamer 2 (VEGF746CaP_5s31). FIG. 5C shows the result obtained regarding the aptamer 3 (VEGF746CaP_5 s49). FIG. 5D shows the result obtained regarding the aptamer 4 (VEGF746CaP_5 s62). FIG. 5E shows the result obtained regarding the aptamer 5 (VEGF746CaP_R8m49). The horizontal axis indicates the time (sec) elapsed after the start of the sample injection, and the vertical axis indicates the signal intensity (RU). As can be seen in FIGS. 5A to 5E, the aptamers 1 to 5 all exhibited binding properties to the VEGF165 in the presence of calcium ions. Further, the signal intensities exhibited by the aptamers 1 to 5 increased as the concentration of the VEGF165 became higher. These results demonstrate that the aptamers 1 to 5 all bind to VEGF165 also in the presence of calcium ions, for example.

Further, from the results of the SPR analysis shown in FIGS. 5A to 5E, the kinetic parameter was calculated. As a result, it was found that the dissociation constants (KD) of the aptamers 1 to 5 against the VEGF165 in the presence of calcium ions were 6.02×10$^{-17}$, 3.66×10$^{-17}$, 2.17×10$^{-21}$, 3.32×10$^{-16}$, and 2.16×10$^{-16}$ mol/L, respectively, and the aptamers 1 to 5 all exhibited excellent binding properties.

Example 3

The present example examined the binding properties of the aptamers of the present invention to VEGF at 37° C. in the absence of calcium ions and in the presence of calcium ions.

First, the binding properties of the aptamers were analyzed using the VEGF sample in the same manner as in Example 1, except that the concentration of the VEGF165 in the sample was set to 1 nmol/L and the SPR was performed at 37° C.

Figure 6A:
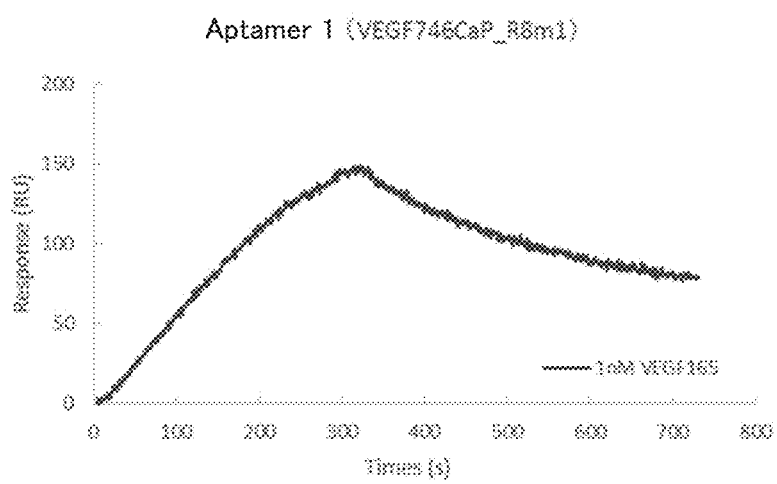
FIGS. 6A to 6E are graphs respectively showing the binding properties of the aptamers 1 to 5 to VEGF165 at 37° C. in Example 3 of the present invention.
Figure 6B:
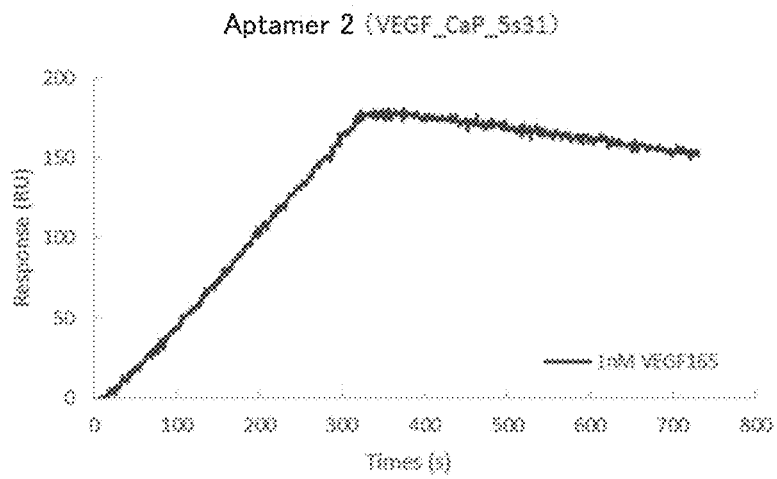
Figure 6C:
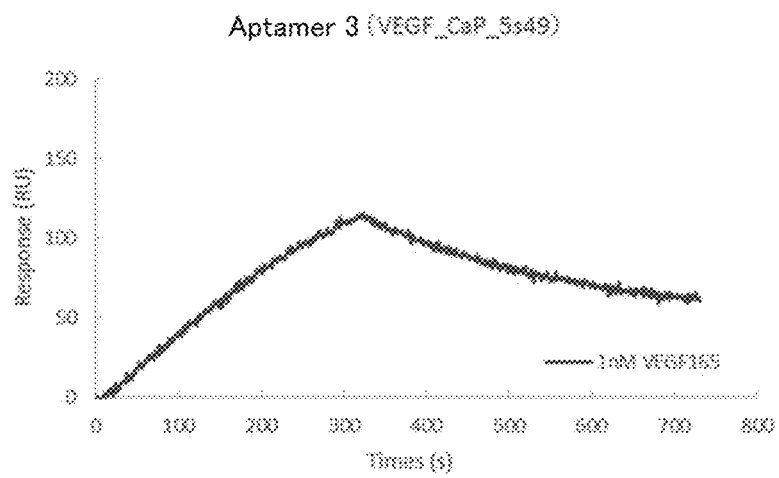
Figure 6D:
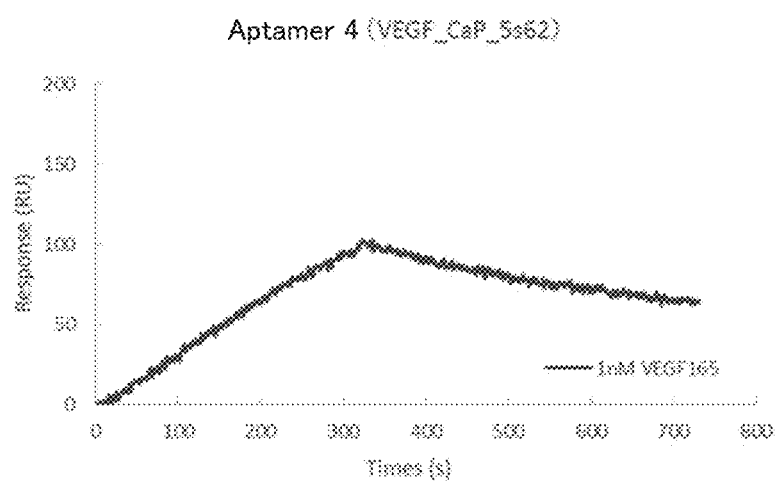
Figure 6E:
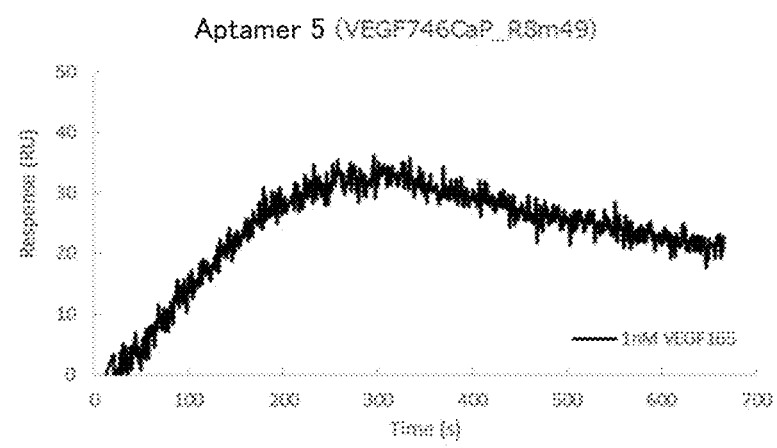

The results obtained are shown in FIGS. 6A to 6E. FIGS. 6A to 6E are graphs respectively showing the binding properties of the aptamers 1 to 5 to the VEGF165 in the absence of calcium ions at 37° C. FIG. 6A shows the result obtained regarding the aptamer 1 (VEGF746CaP_R8m1). FIG. 6B shows the result obtained regarding the aptamer 2 (VEGF746CaP_5s31). FIG. 6C shows the result obtained regarding the aptamer 3 (VEGF746CaP_5 s49). FIG. 6D shows the result obtained regarding the aptamer 4 (VEGF746CaP_5 s62). FIG. 6E shows the result obtained regarding the aptamer 5 (VEGF746CaP_R8m49). The horizontal axis indicates the time (sec) elapsed after the start of the sample injection, and the vertical axis indicates the signal intensity (RU). As can be seen in FIGS. 6A to 6E, the aptamers 1 to 5 all exhibited binding properties to the VEGF165 in the absence of calcium ions at 37° C.

Next, the binding properties of the aptamers were analyzed using the VEGF sample in the same manner as in Example 2, except that the concentration of the VEGF165 in the sample was set to 1 nmol/L and the SPR was performed at 37° C.

Figure 7A:
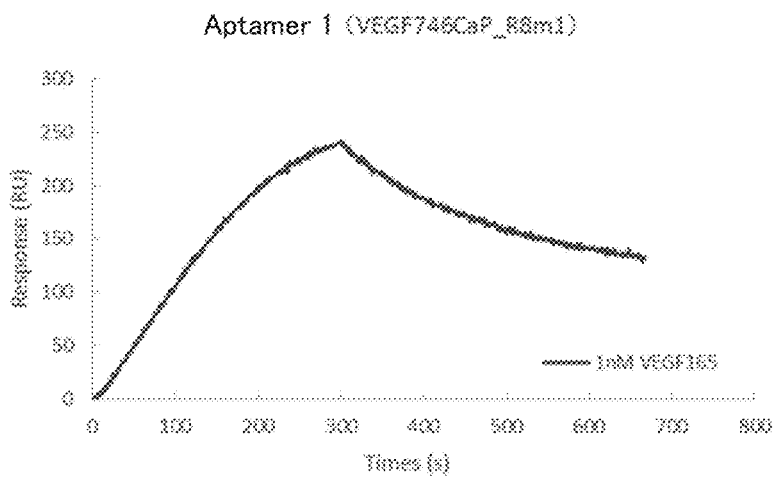
FIGS. 7A to 7E are graphs respectively showing the binding properties of the aptamers 1 to 5 to VEGF165 at 37° C. in the presence of calcium ions in Example 3 of the present invention.
Figure 7B:
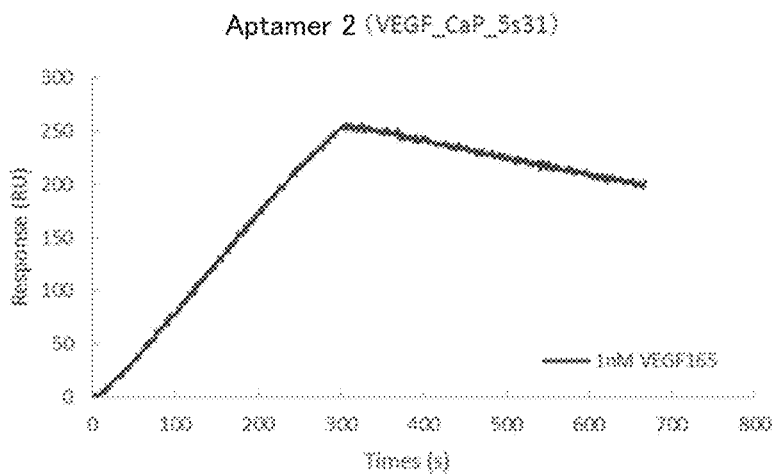
Figure 7C:
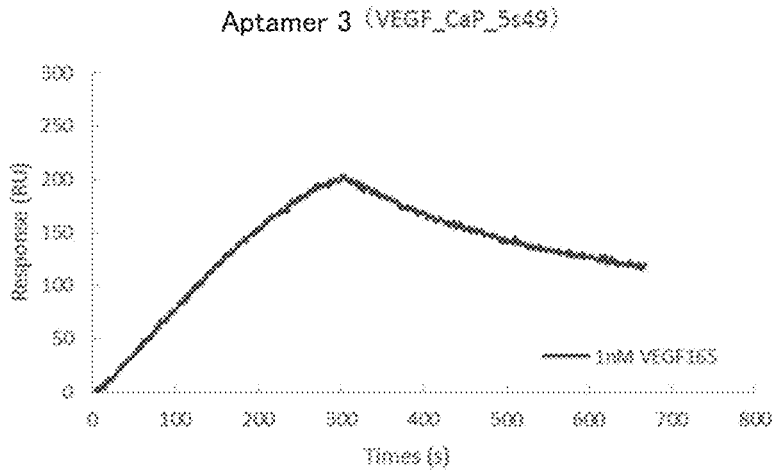
Figure 7D:
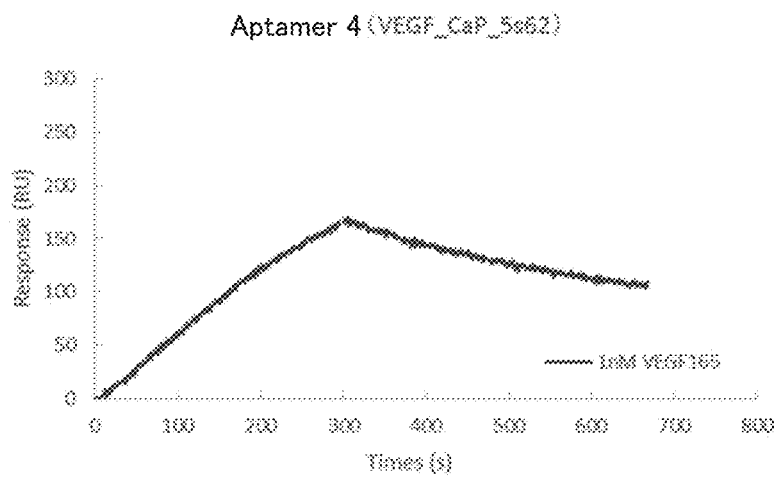
Figure 7E:
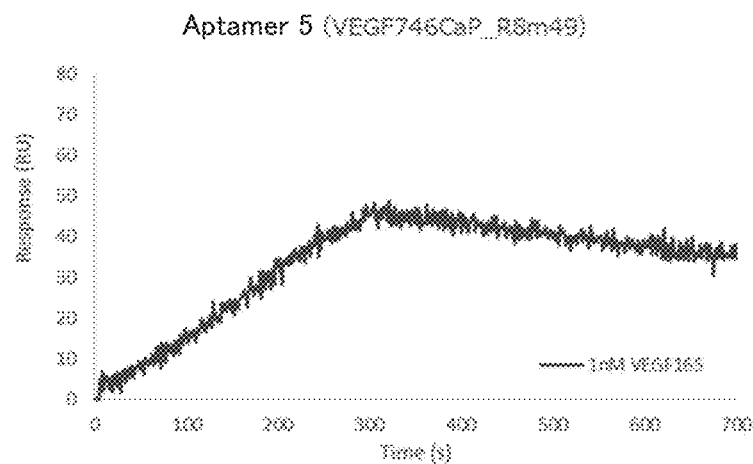

The results obtained are shown in FIGS. 7A to 7E. FIGS. 7A to 7E are graphs respectively showing the binding properties of the aptamers 1 to 5 to the VEGF165 in the presence of calcium ions at 37° C. FIG. 7A shows the result obtained regarding the aptamer 1 (VEGF746CaP_R8m1). FIG. 7B shows the result obtained regarding the aptamer 2 (VEGF746CaP_5s31). FIG. 7C shows the result obtained regarding the aptamer 3 (VEGF746CaP_5 s49). FIG. 7D shows the result obtained regarding the aptamer 4 (VEGF746CaP_5 s62). FIG. 7E shows the result obtained regarding the aptamer 5 (VEGF746CaP_R8m49). The horizontal axis indicates the time (sec) elapsed after the start of the sample injection, and the vertical axis indicates the signal intensity (RU). As can be seen in FIGS. 7A to 7E, the aptamers 1 to 5 all exhibited binding properties to the VEGF165 in the presence of calcium ions at 37° C.

The above results demonstrate that the aptamers 1 to 5 all can bind to VEGF165 when they are used in living organisms, for example.

Example 4

The present example examined through SPR analysis whether VEGFs bound to the aptamers of the present invention further can bind to VEGF receptors.

The aptamers 1 to 5 were used as aptamers, and the VEGF sample and a VEGF receptor sample were used as samples. The VEGF receptor sample was prepared in the same manner as the VEGF sample, except that a VEGF receptor (R&D systems, Cat. No: 357-KD-050/CF) was used instead of the VEGF.

The analysis of binding properties by SPR was carried out in the following manner. First, biotinylated poly(dT) was bound to the sensor chip and each of the poly(dA)-added aptamers was then bound to the chip in the same manner as in Example 1. Subsequently, the 5 nmol/L VEGF sample was injected using an SB1T buffer at a flow rate of 50 μL/min for 240 seconds (first injection), followed by washing performed by flowing the SB1T buffer under the same conditions. Thereafter, the 5 nmol/L VEGF receptor sample was injected using an SB1T buffer at a flow rate of 50 μL/min for 240 seconds (second injection), followed by washing performed by flowing the SB1T buffer under the same conditions. With the time at which the first injection was started being 0 seconds, the signal intensity after the sample injection was measured. The SPR was carried out at 25° C. Also, analysis of binding properties by SPR was carried out in the same manner, except that the first and second injections were performed using the combinations shown in Table 1 below instead of the combination of the VEGF sample and the VEGF receptor sample.

TABLE 1

|  | First injection | Second injection |
| --- | --- | --- |
| Example | 5 nM VEGF | 5 nM VEGF receptor |
| Control 1 | 5 nM VEGF | SB1T buffer |
| Control 2 | 5 nM VEGF receptor | SB1T buffer |
| Control 3 | SB1T buffer | 5 nM VEGF receptor |

Figure 8A:
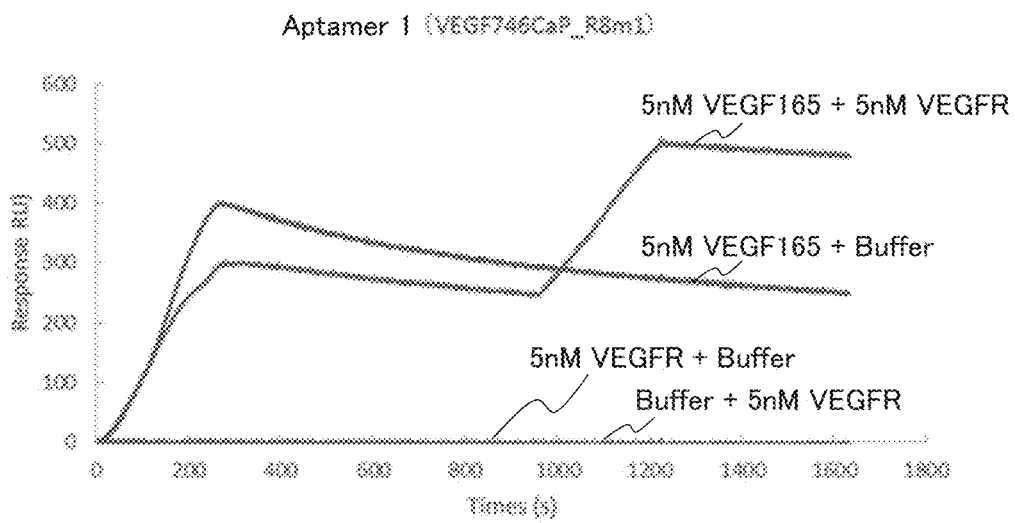
FIGS. 8A to 8E are graphs respectively showing the binding properties of the aptamers 1 to 5 in Example 4 of the present invention.
Figure 8B:
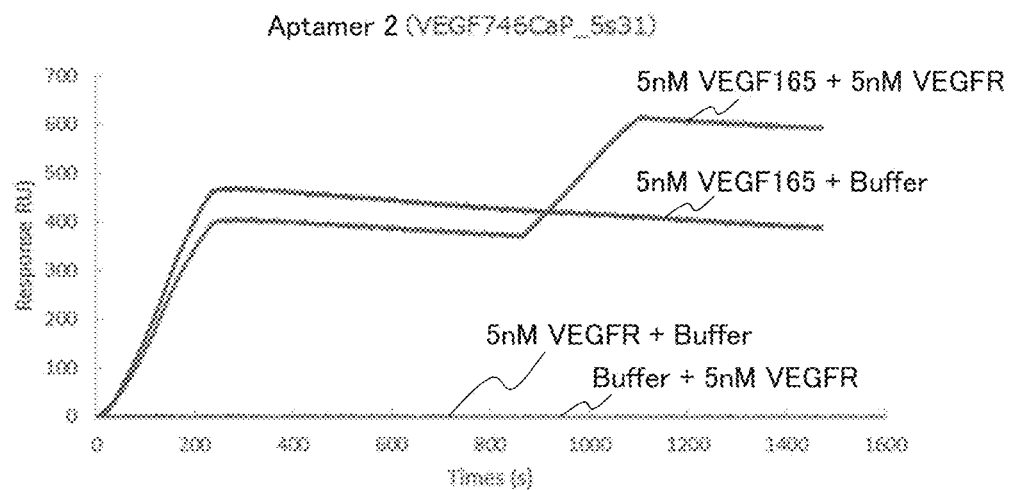
Figure 8C:
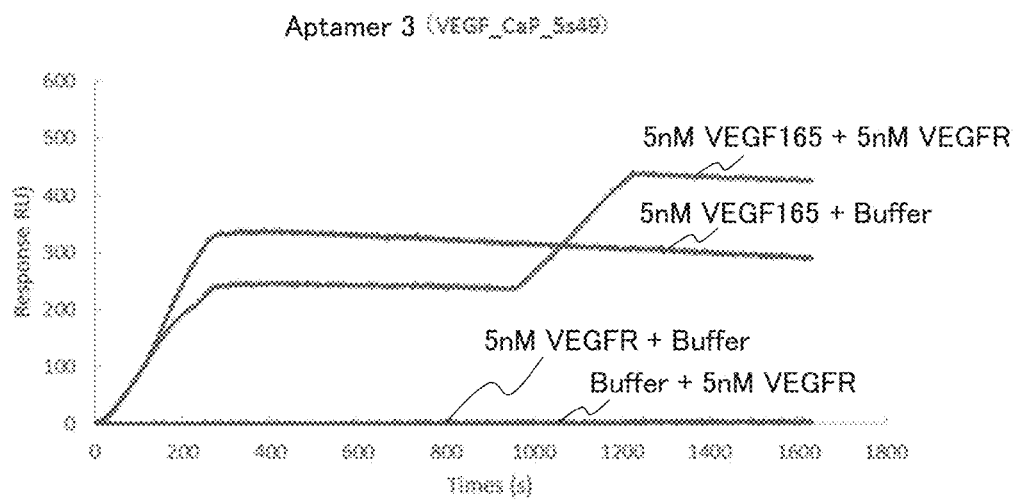

The results obtained are shown in FIGS. 8A to 8E. FIGS. 8A to 8E are graphs respectively showing the binding properties of the aptamers 1 to 5 to the samples. FIG. 8A shows the result obtained regarding the aptamer 1 (VEGF746CaP_R8m1). FIG. 8B shows the result obtained regarding the aptamer 2 (VEGF746CaP_5s31). FIG. 8C shows the result obtained regarding the aptamer 3

Figure 8D:
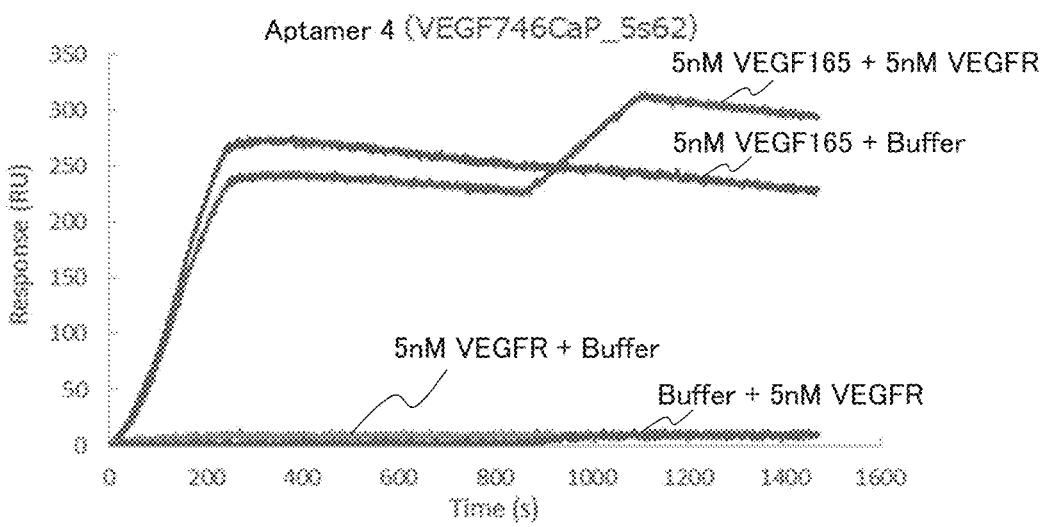
Figure 8E:
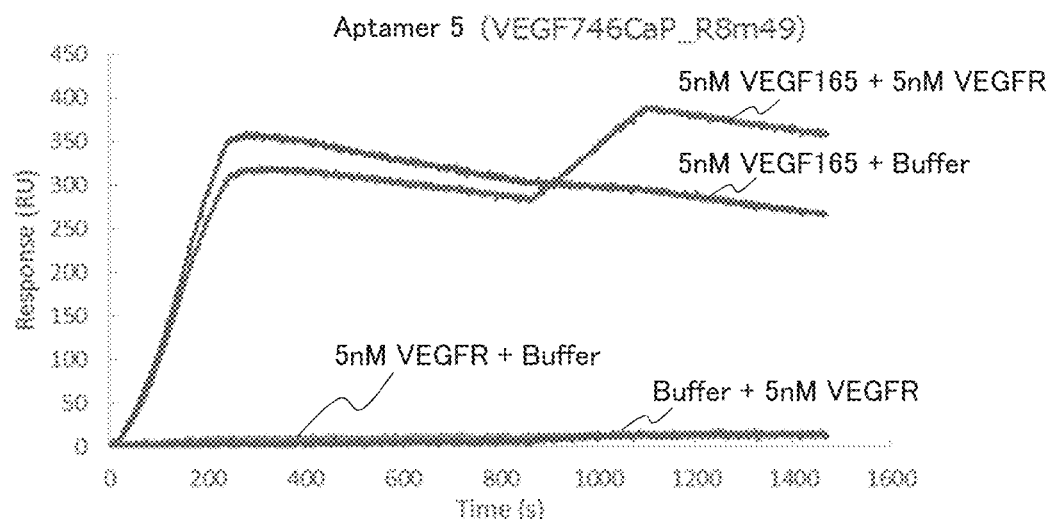

(VEGF746CaP_5s49). FIG. 8D shows the result obtained regarding the aptamer 4 (VEGF746CaP_5s62). FIG. 8E shows the result obtained regarding the aptamer 5 (VEGF746CaP_R8m49). The horizontal axis indicates the time (sec) elapsed after the start of the first injection, and the vertical axis indicates the signal intensity (RU). As can be seen in FIGS. 8A to 8E, the aptamers 1 to 5 exhibited increase in signal intensity when the VEGF sample was injected in the first injection. That is, the aptamers 1 to 5 exhibited binding properties to the VEGF165. Further, the aptamers 1 to 5 also exhibited increase in signal intensity when the VEGF receptor sample was injected in the second injection. That is, the VEGF165 bound to the aptamers 1 to 5 exhibited binding properties to the VEGF receptors.

In contrast, in the case where the injections were performed using the combination of control 1 shown in Table 1, the aptamers 1 to 5 exhibited increase in signal intensity when the VEGF sample was injected in the first injection. However, when the SB1T buffer was injected in the second injection, increase in signal intensity was not observed. That is, the VEGF165 bound to the aptamers 1 to 5 did not exhibit binding properties to the SB1T buffer.

In the case where the injections were performed using the combination of control 2 shown in Table 1, the aptamers 1 to 5 did not exhibit increase in signal intensity when the VEGF receptor sample was injected in the first injection. That is, the aptamers 1 to 5 did not exhibit binding properties to VEGF receptors. Further, the aptamers 1 to 5 also did not exhibit increase in signal intensity when the SB1T buffer was injected in the second injection.

When the injections were performed using the combination of control 3 shown in Table 1, the aptamers 1 to 5 did not exhibit increase in signal intensity when the SB1T buffer was injected in the first injection. That is, the aptamers 1 to 5 did not exhibit binding properties to the SB1T buffer. Further, the aptamers 1 to 5 also did not exhibit increase in signal intensity when the VEGF receptor sample was injected in the second injection.

The above results demonstrate that VEGFs bound to the aptamers 1 to 5 further bind to VEGF receptors.

Example 5

The present example examined whether VEGFs bound to the aptamers of the present invention can phosphorylate VEGF receptors.

Phosphorylation of VEGF receptors was measured using the Phospho-VEGF R2/KDR (Catalog No.: DYC1766, R&D systems) according to the manufacturer's protocol. Antibodies and a substrate solution to be described below were those included in the kit. 24 hours prior to the start of the experiment, a medium (ATCC®, PCS-100-040) containing microvascular endothelial cell growth supplements (ATCC®, PCS-100-030) for HUVEC cells (ATCC®, PCS-100-010) was replaced with a serum-free medium. The VEGF165 (0.01, 0.04, 0.12, 0.37, 1.11, 3.33, 10, or 30 nmol/L) was added to the medium containing the HUVEC cells. The cells were treated with the VEGF165 for 5 minutes. Thereafter the cells were washed with PBS. The amount of phosphorylated VEGF receptor was measured using the Phospho-VEGFR2/KDR according to the manufacturer's protocol.

Figure 9:
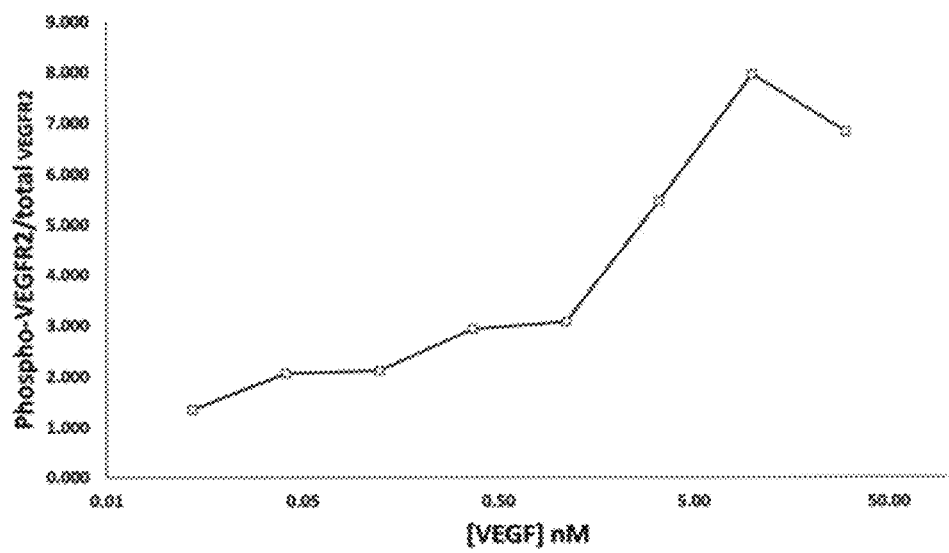
FIG. 9 is a dose response curve for VEGF receptor phosphorylation as a function of VEGF concentration in Example 5 of the present invention.

The results obtained are shown in FIG. 9. FIG. 9 is a dose response curve for VEGF receptor phosphorylation as a function of VEGF165 concentration. The horizontal axis indicates the concentration of the VEGF165, and the vertical axis indicates the proportion of phosphorylated VEGF receptors in the total amount of the VEGF receptors (the value obtained by dividing the measured value of the phosphorylated VEGF receptors by the measured value of the total amount of the VEGF receptors). As can be seen in FIG. 9, when the concentration of the VEGF165 was 10 nmol/L or lower, the proportion of the phosphorylated VEGF receptors increased as the concentration of the VEGF165 became higher. On the other hand, when the concentration of the VEGF165 was higher than 10 nmol/L, the proportion of the phosphorylated VEGF receptors decreased as the concentration of the VEGF165 became higher.

Next, phosphorylation of VEGF receptors was measured in the same manner using the VEGF165 sample, except that the concentration of the VEGF165 in the sample was set to 0, 0.5, 1, or 3 nmol/L. Further, phosphorylation of VEGF receptors was measured in the same manner, except that 1 nmol/L of the aptamer 2 was used in addition to the VEGF165, and the sample was prepared by mixing the VEGF165 sample and the aptamer 2 for 30 minutes. As a control, phosphorylation of VEGF receptors was measured in the same manner, except that the sample was prepared using 1 nmol/L of Pat224 (VEGF aptamer, disclosed in U.S. Pat. No. 5,811,533) and 1 nmol/L of Macugen (VEGF receptor inhibitor, Bausch+Lomb).

Figure 10:
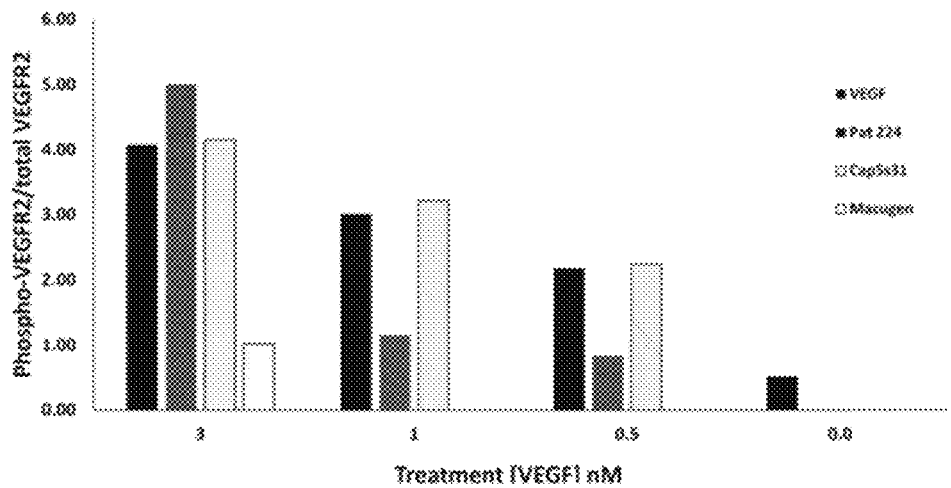
FIG. 10 is a graph showing the phosphorylation of VEGF receptors in Example 5 of the present invention.

The results obtained are shown in FIG. 10. FIG. 10 is a graph showing the phosphorylation of the VEGF receptors by the VEGF165. The horizontal axis indicates the concentration of the VEGF165, and the vertical axis indicates the proportion of phosphorylated VEGF receptors in the total amount of the VEGF receptors. As can be seen in FIG. 10, the proportion of the phosphorylated VEGF receptors increased as the concentration of the VEGF165 became higher. The proportion of the phosphorylated VEGF receptors in the sample containing the aptamer 2 (Cap5s31) was roughly equivalent to that in the sample containing the VEGF165 only. This revealed that the aptamer 2 does not inhibit phosphorylation of VEGF receptors by VEGF165. In contrast, in the sample containing the Macugen, the proportion of the phosphorylated VEGF receptors was much lower than those in the sample containing the VEGF165 only over the entire concentration range of the VEGF165. That is, Macugen, which is a VEGF receptor inhibitor, inhibited the phosphorylation of the VEGF receptors by the VEGF165. Further, in the sample containing the Pat224, the proportion of the phosphorylated VEGF receptors was much lower than that in the sample containing the VEGF165 only, when the concentration of VEGF165 was 1, or 0.5 nmol/L. That is, Pat224, which is the VEGF aptamer, inhibited phosphorylation of the VEGF receptors by the VEGF165 when the concentration of the VEGF165 was 1 nmol/L or lower.

Next, the phosphorylation of VEGF receptors was measured using the VEGF165 sample in the same manner, except that: the concentration of the VEGF165 in the sample was set to 1 nmol/L; in addition to the VEGF165, the aptamers 1 and 2 were used as aptamers; and the concentration of each of the aptamers in the sample was set to 7.81, 15.63, 31.25, 62.5, 125, 250, 500, or 1000 nmol/L.

Figure 11:
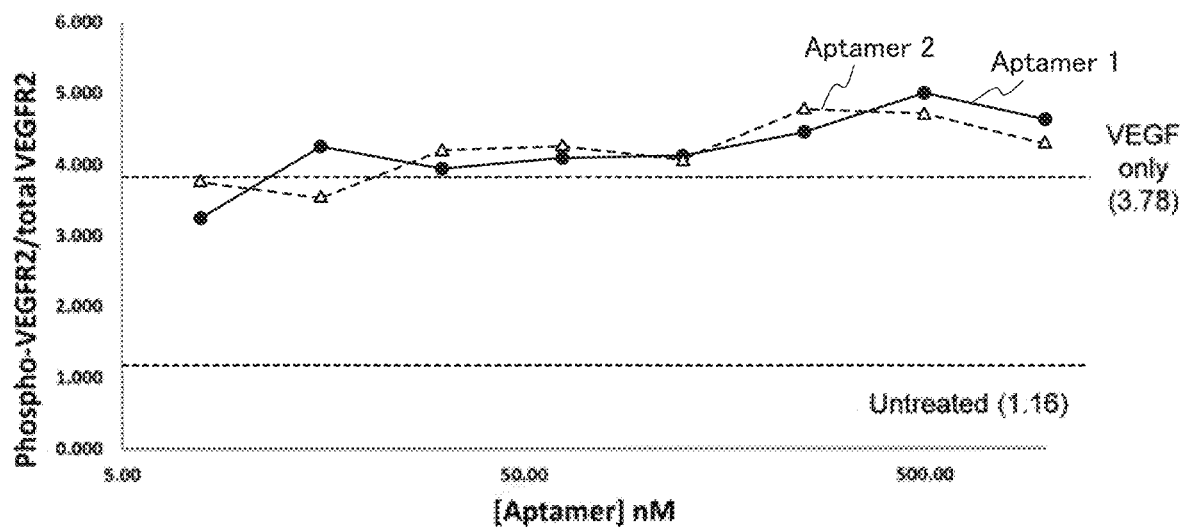
FIG. 11 is a graph showing the phosphorylation of VEGF receptors after treatment of cells with VEGF in the presence of aptamers in Example 5 of the present invention.

The results obtained are shown in FIG. 11. FIG. 11 is a graph showing the phosphorylation of the VEGF receptors after the treatment of the cells with the VEGF165 in the presence of the respective aptamers. The horizontal axis indicates the concentration of each aptamer, and the vertical axis indicates the proportion of phosphorylated VEGF receptors in the total amount of the VEGF receptors.

As indicated in FIG. 11, the proportion of the phosphorylated VEGF receptors was 3.78 in the sample containing the VEGF165 only and 1.16 in the VEGF165-free sample. In the sample containing the aptamer 1, the proportion of the phosphorylated VEGF receptors was roughly equivalent to or higher than that in the sample containing the VEGF165 only over the entire concentration range of the aptamer 1. In the sample containing the aptamer 2, the proportion of the phosphorylated VEGF receptors was roughly equivalent to or higher than that in the sample containing the VEGF165 only over the entire concentration range of the aptamer 2.

Phosphorylation of VEGF receptors was measured using the VEGF165 sample in the same manner, except that the aptamers 2 and 3 were used as aptamers and the concentration of each of the aptamers in the sample was set to 0.01, 0.06, 0.32, 1.6, 8, 40, 200, or 1000 nmol/L.

Figure 12:
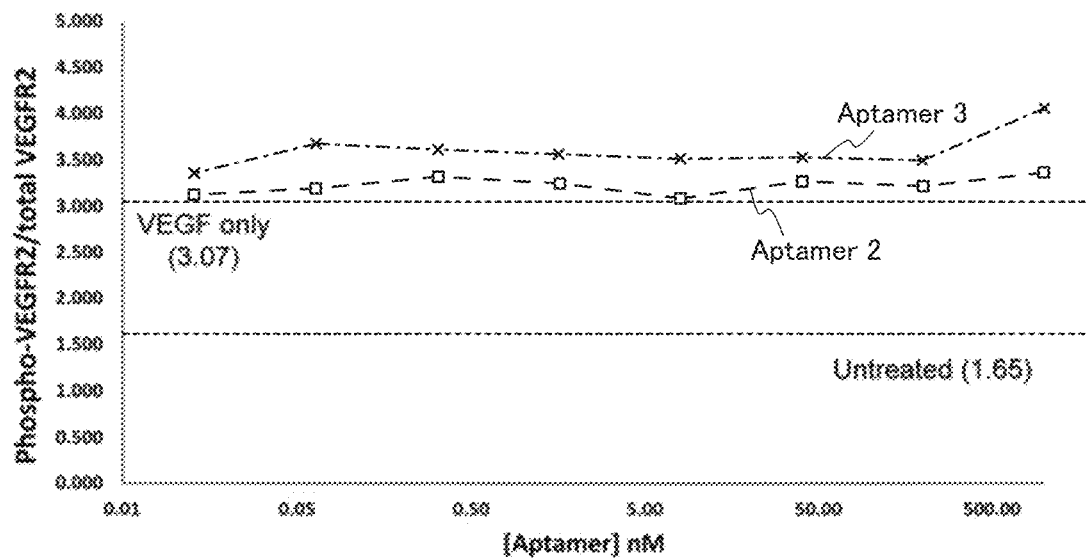
FIG. 12 is a graph showing the phosphorylation of VEGF receptors after treatment of cells with VEGF in the presence of aptamers in Example 5 of the present invention.

The results obtained are shown in FIG. 12. FIG. 12 is a graph showing the phosphorylation of the VEGF receptors after the treatment of the cells with the VEGF165 in the presence of the respective aptamers. The horizontal axis indicates the concentration of each aptamer, and the vertical axis indicates the proportion of phosphorylated VEGF receptors in the total amount of the VEGF receptors.

As indicated in FIG. 12, the proportion of the phosphorylated VEGF receptors was 3.07 in the sample containing the VEGF165 only and 1.65 in the VEGF165-free sample. In the sample containing the aptamer 2, the proportion of the phosphorylated VEGF receptors was roughly equivalent to or higher than that in the sample containing the VEGF165 only over the entire concentration range of the aptamer 2. In the sample containing the aptamer 3, the proportion of the phosphorylated VEGF receptors was roughly equivalent to or higher than that in the sample containing the VEGF165 only over the entire concentration range of the aptamer 3.

The above results demonstrate that VEGF165 can phosphorylate VEGF receptors on cell surfaces under conditions where all VEGF165 is expected to be bound by the aptamers 1, 2, and 3 respectively.

While the present invention has been described above with reference to example embodiments, the present invention is by no means limited thereto. Various changes and modifications that may become apparent to those skilled in the art may be made in the configuration and specifics of the present invention without departing from the scope of the present invention.

INDUSTRIAL APPLICABILITY

The present invention can provide a method for producing a nucleic acid molecule that can obtain a nucleic acid molecule that binds to a target and does not inhibit a function of the target. The present invention is a very useful tool in the field of pharmaceuticals and the like, for example.

A part of or the whole of the above-described embodiments can be described as the following supplementary notes. However, the present invention is by no means limited thereto.

(Supplementary Note 1)

A method for producing a nucleic acid molecule that binds to a first biological molecule and does not inhibit a function of the first biological molecule, the method including the steps of:

(A) bringing a candidate nucleic acid molecule into contact with the first biological molecule to select a nucleic acid molecule that has bound to the first biological molecule as a first selected nucleic acid molecule; and (B) selecting the first selected nucleic acid molecule as an intended nucleic acid molecule.

(Supplementary Note 2)

The method according to supplementary note 1, further including, after the step (A), the step of:

(C) bringing a second biological molecule into contact with a complex of the first selected nucleic acid molecule and the first biological molecule to detect a function of the second biological molecule, wherein after the step (C), in the step (B), the first selected nucleic acid molecule of the complex with which the function of the second biological molecule is detected is selected as an intended nucleic acid molecule.

(Supplementary Note 3)

The method according to supplementary note 2, wherein the function of the first biological molecule is a function of binding to the second biological molecule.

(Supplementary Note 4)

The method according to supplementary note 3, wherein the function of the first biological molecule is a function of regulating activity of the second biological molecule by binding to the second biological molecule.

(Supplementary Note 5)

The method according to any one of supplementary notes 2 to 4, wherein the first biological molecule is a protein and the second biological molecule is a receptor.

(Supplementary Note 6)

The method according to supplementary note 5, wherein the protein is a growth factor.

(Supplementary Note 7)

The method according to supplementary note 6, wherein the growth factor is VEGF.

(Supplementary Note 8)

The method according to any one of supplementary notes 1 to 7, wherein in the step (A), the candidate nucleic acid molecule is brought into contact with the first biological molecule, which is a target substance, and a non-target substance, and the nucleic acid molecule that has bound to the target substance and has not bound to the non-target substance is selected as the first selected nucleic acid molecule.

(Supplementary Note 9)

The method according to supplementary note 8, wherein the non-target substance is the second biological molecule to which the first biological molecule binds.

(Supplementary Note 10)

The method according to supplementary note 9, wherein the non-target substance is a polypeptide including a sequence corresponding to a binding site of an amino acid sequence of the second biological molecule with the first biological molecule.

(Supplementary Note 11)

The method according to supplementary note 8, wherein the non-target substance is a polypeptide including a sequence corresponding to a binding site of an amino acid sequence of the first biological molecule with the second biological molecule.

(Supplementary Note 12)

The method according to supplementary note 11, wherein the target substance is a polypeptide that includes a sequence ($S_R$) corresponding to a binding site of an amino acid sequence of the first biological molecule with the second biological molecule and also includes a freely-selected nucleic acid binding sequence ($S_A$) that is different from the sequence corresponding to the binding site with the second biological molecule and the non-target substance is a polypeptide that includes the sequence ($S_R$) and does not include the nucleic acid binding sequence ($S_A$).

(Supplementary Note 13)

The method according to supplementary note 11 or 12, wherein the target substance and the non-target substance are proteins in a splicing variant relationship with each other.

(Supplementary Note 14)
The method according to any one of supplementary notes 8 to 13, wherein
the target substance is an intended protein and the non-target substance is a protein other than the intended protein.

(Supplementary Note 15) The method according to supplementary note 14, wherein
the target substance is an intended growth factor and the non-target substance is a growth factor other than the intended growth factor.

(Supplementary Note 16)
The method according to supplementary note 15, wherein the nucleic acid binding sequence ($S_A$) is a sequence including a heparin binding domain (HBD).

(Supplementary Note 17)
The method according to supplementary note 16, wherein
the intended growth factor is VEGF165 and the growth factor other than the intended growth factor is VEGF121.

(Supplementary Note 18)
A nucleic acid molecule that binds to VEGF, the nucleic acid molecule including:
any one of the following polynucleotides (a) and (b):
(a) a polynucleotide that consists of a base sequence of SEQ ID NO: 1 or a partial sequence of the base sequence of SEQ ID NO: 1; and
(b) a polynucleotide that consists of a base sequence having at least 80% identity to the base sequence of the polynucleotide (a), binds to VEGF, and does not inhibit a function of the VEGF.

(Supplementary Note 19) The nucleic acid molecule according to supplementary note 18, wherein
the function of the VEGF is a function of binding to a VEGF receptor.

(Supplementary Note 20)
The nucleic acid molecule according to supplementary note 19, wherein
the function of the VEGF is a function of regulating activity of the VEGF receptor by binding to the VEGF receptor.

(Supplementary Note 21)
The nucleic acid molecule according to any one of supplementary notes 18 to 20, wherein
the partial sequence of the base sequence of SEQ ID NO: 1 is at least one base sequence selected from the group consisting of SEQ ID NOs: 2 to 4.

(Supplementary Note 22)
The nucleic acid molecule according to any one of supplementary notes 18 to 20, wherein
the polynucleotide (b) is a polynucleotide consisting of a base sequence of SEQ ID NO: 7.

(Supplementary Note 23) The nucleic acid molecule according to any one of supplementary notes 18 to 20, wherein
the polynucleotide (b) is the following polynucleotide (b1):
(b1) a polynucleotide that consists of a base sequence having at least 80% identity to the base sequence of the polynucleotide (a), includes a base sequence of any one of SEQ ID NOs: 2 to 4, binds to the VEGF, and does not inhibit the function of the VEGF.

(Supplementary Note 24)
The nucleic acid molecule according to any one of supplementary notes 18 to 20, wherein
the polynucleotide (b) is the following polynucleotide (b2):
(b2) a polynucleotide that consists of a base sequence having at least 80% identity to the base sequence of the polynucleotide (a), can form a secondary structure represented by any one of the following formulae (1) to (5), binds to the VEGF, and does not inhibit the function of the VEGF.

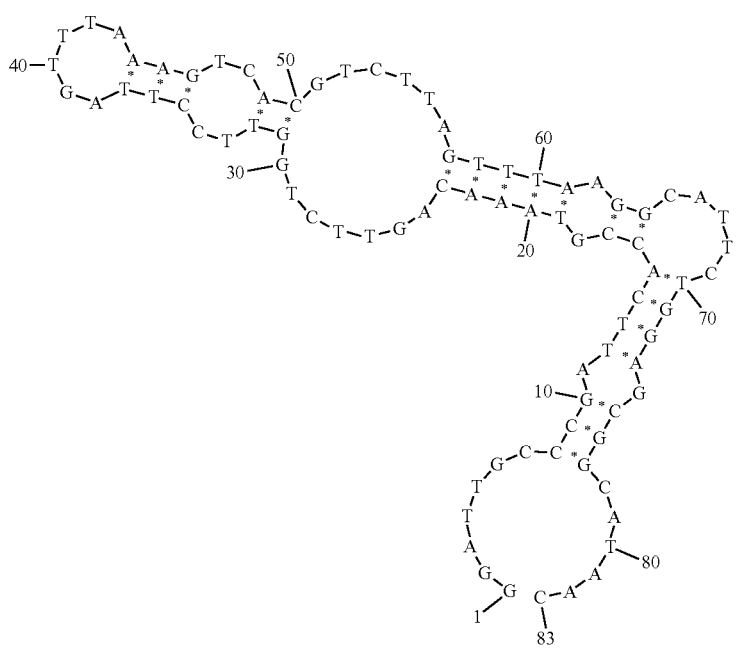

(1)

-continued (2)
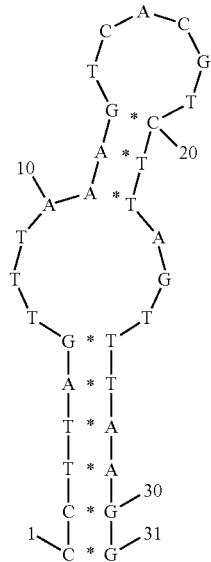

(3)
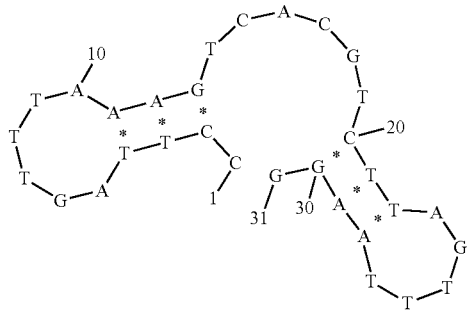

(4)
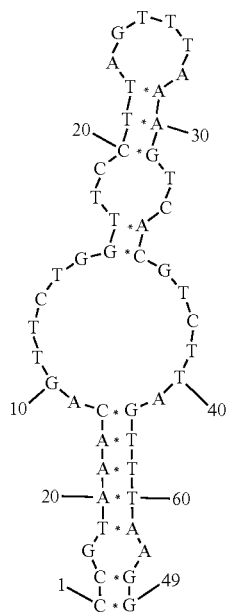

(5)
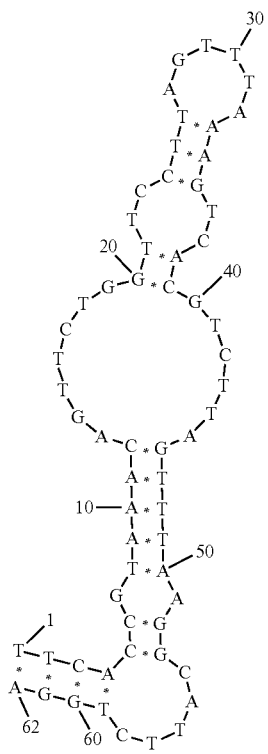

(Supplementary Note 25)

The nucleic acid molecule according to any one of supplementary notes 18 to 20, wherein
 the polynucleotide (b) is the following polynucleotide (b3):
 (b3) a polynucleotide that consists of a base sequence having at least 80% identity to the base sequence of the polynucleotide (a), includes a base sequence of at least one of SEQ ID NOs: 5 and 6, binds to the VEGF, and does not inhibit the function of the VEGF.

(Supplementary Note 26)

The nucleic acid molecule according to any one of supplementary notes 18 to 20, wherein
 the polynucleotide is DNA.

(Supplementary Note 27)

A biomaterial including:
 a binding nucleic acid molecule; and
 a carrier,
 the binding nucleic acid molecule being bound to the carrier,
 wherein the binding nucleic acid molecule binds to a predetermined protein and does not inhibit a function of the predetermined protein.

(Supplementary Note 28)
The biomaterial according to supplementary note 27, wherein
the function of the predetermined protein is a function of binding to a receptor for the protein.
(Supplementary Note 29)
The biomaterial according to supplementary note 28, wherein
the function of the predetermined protein is a function of regulating activity of the receptor by binding to the receptor.
(Supplementary Note 30)
The biomaterial according to any one of supplementary notes 27 to 29, wherein
the predetermined protein is a growth factor.
(Supplementary Note 31)
The biomaterial according to supplementary note 30, wherein
the growth factor is VEGF.
(Supplementary Note 32)
The biomaterial according to supplementary note 31, wherein
the binding nucleic acid molecule is the binding nucleic acid molecule according to any one of supplementary notes 18 to 26.
(Supplementary Note 33)
The biomaterial according to any one of supplementary notes 27 to 32, wherein
the binding nucleic acid molecule is bound to the carrier via an additional sequence.
(Supplementary Note 34)
The biomaterial according to any one of supplementary notes 27 to 33, wherein
the carrier is a polymer.
(Supplementary Note 35)
The biomaterial according to supplementary note 34, wherein
the polymer is a gel.
(Supplementary Note 36)
The biomaterial according to any one of supplementary notes 27 to 35, which is a biological scaffold.
(Supplementary Note 37)
A method for producing a biomaterial, the method including the step of:
binding a binding nucleic acid molecule to a carrier, wherein the binding nucleic acid molecule binds to a predetermined protein and does not inhibit a function of the predetermined protein.
(Supplementary Note 38)
The method according to supplementary note 37, further including the step of:
binding the predetermined protein to the binding nucleic acid molecule.
(Supplementary Note 39)
The method according to supplementary note 37 or 38, wherein
the function of the predetermined protein is a function of binding to a receptor for the protein.
(Supplementary Note 40)
The method according to supplementary note 39, wherein
the function of the predetermined protein is a function of regulating activity of the receptor by binding to the receptor.
(Supplementary Note 41)
The method according to any one of supplementary notes 37 to 40, wherein
the predetermined protein is a growth factor.
(Supplementary Note 42)
The method according to supplementary note 41, wherein
the growth factor is VEGF.
(Supplementary Note 43)
The method according to supplementary note 42, wherein
the binding nucleic acid molecule is the binding nucleic acid molecule according to any one of supplementary notes 18 to 26.
(Supplementary Note 44)
The method according to any one of supplementary notes 37 to 43, wherein
the binding nucleic acid molecule is caused to bind to the carrier via an additional sequence.
(Supplementary Note 45)
The method according to any one of supplementary notes 37 to 44, wherein
the carrier is a biodegradable polymer.
(Supplementary Note 46)
The method according to supplementary note 45, wherein
the biodegradable polymer is a gel.
(Supplementary Note 47)
The method according to any one of supplementary notes 37 to 46, wherein
the biomaterial is a biological scaffold.

What is claimed is:

1. A biomaterial comprising:
   a binding nucleic acid molecule; and
   a carrier,
   the binding nucleic acid molecule being bound to the carrier,
   wherein the binding nucleic acid molecule binds to a predetermined protein and does not inhibit a function of the predetermined protein,
   the nucleic acid molecule including:
   any one of the following polynucleotides (a) and (b):
   (a) a polynucleotide that consists of a base sequence of SEQ ID NO: 1 or a partial sequence of the base sequence of SEQ ID NO: 1, and
   (b) a polynucleotide that consists of a base sequence having at least 80% identity to the base sequence of the polynucleotide (a), binds to the predetermined protein, and does not inhibit a function of the predetermined protein.

2. The biomaterial according to claim 1, wherein the function of the predetermined protein is a function of binding to a receptor for the protein.

* * * * *